US009664923B2

(12) United States Patent
Wildsmith et al.

(10) Patent No.: US 9,664,923 B2
(45) Date of Patent: May 30, 2017

(54) LENS PRECURSOR WITH FEATURES FOR THE FABRICATION OF AN OPHTHALMIC LENS

(71) Applicant: Johnson & Johnson Vision Care, Inc., Jacksonville, FL (US)

(72) Inventors: Christopher Wildsmith, Jacksonville, FL (US); Michael Widman, Jacksonville, FL (US); P. Mark Powell, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 404 days.

(21) Appl. No.: 14/110,265

(22) PCT Filed: Jun. 28, 2013

(86) PCT No.: PCT/US2013/048572
§ 371 (c)(1),
(2) Date: Oct. 7, 2013

(87) PCT Pub. No.: WO2014/005020
PCT Pub. Date: Jan. 3, 2014

(65) Prior Publication Data
US 2014/0055744 A1 Feb. 27, 2014

Related U.S. Application Data

(60) Provisional application No. 61/665,973, filed on Jun. 29, 2012.

(51) Int. Cl.
*G02C 7/02* (2006.01)
*B29D 11/00* (2006.01)
*B29C 67/00* (2017.01)

(52) U.S. Cl.
CPC ............ *G02C 7/024* (2013.01); *B29C 67/007* (2013.01); *B29D 11/00134* (2013.01); *G02C 7/02* (2013.01)

(58) Field of Classification Search
CPC ... B29C 67/007; B29D 11/00134; G02C 7/02; G02C 7/024
(Continued)

(56) References Cited

U.S. PATENT DOCUMENTS 3,902,693 A * 9/1975 Crandon .......... B29D 11/00413
249/105
4,190,621 A * 2/1980 Greshes ........... B29D 11/00028
264/1.8
(Continued)

FOREIGN PATENT DOCUMENTS

EP 2228201 A2 9/2010
EP 2228202 A2 9/2010
(Continued)

OTHER PUBLICATIONS

Written Opinion for corresponding Application No. PCTUS2013048572 date of issuance Dec. 31, 2014.
(Continued)

*Primary Examiner* — Alison L Hindenlang
*Assistant Examiner* — Emmanuel S Luk

(57) ABSTRACT

This invention provides for the fabrication of ophthalmic lenses via the utilization of DMD shows and/or DMD files. More specifically, the use of the DMD shows and/or DMD files to generate lens precursor designs comprising described features to form part of a substructure for the fluid reactive media portion of the lens precursor and wherein the lens precursor can generate particular ophthalmic lens designs in a free-form manner using methods described herein.

8 Claims, 20 Drawing Sheets

(58) Field of Classification Search
USPC .......................................................... 425/808
See application file for complete search history.

(56) References Cited

U.S. PATENT DOCUMENTS

| | | | | |
|---|---|---|---|---|
| 4,208,364 | A | | 6/1980 | Shepherd |
| 4,284,399 | A | * | 8/1981 | Newcomb ........... B29C 33/0038 249/117 |
| 4,383,673 | A | * | 5/1983 | Laprade ................. B29D 12/02 249/142 |
| 4,865,779 | A | * | 9/1989 | Ihn ................... B29D 11/00057 249/142 |
| 4,955,580 | A | * | 9/1990 | Seden .................. A45C 11/005 249/82 |
| 5,271,875 | A | * | 12/1993 | Appleton ............ B29C 33/0038 249/160 |
| 5,326,505 | A | * | 7/1994 | Adams ................ B29C 33/0055 264/1.36 |
| 6,405,993 | B1 | * | 6/2002 | Morris ............. B29D 11/00057 249/141 |
| 6,444,145 | B1 | * | 9/2002 | Clutterbuck ..... B29D 11/00057 249/117 |
| 6,475,410 | B1 | * | 11/2002 | Nakagawa .......... B29C 33/3842 264/2.2 |
| 6,565,776 | B1 | * | 5/2003 | Li ........................... B29C 33/56 249/114.1 |
| 6,627,124 | B1 | * | 9/2003 | Herbrechtsmeier ....................... B29C 35/0888 264/1.1 |
| 6,710,945 | B1 | * | 3/2004 | Miranda ................ G02B 7/021 359/811 |
| 7,320,587 | B2 | | 1/2008 | Goodenough ... B29D 11/00038 425/192 R |
| 7,731,872 | B2 | * | 6/2010 | Bruce ................... B29C 33/202 156/73.1 |
| 7,731,873 | B2 | * | 6/2010 | Darnton ........... B29D 11/00038 264/1.36 |
| 8,313,675 | B2 | * | 11/2012 | Plaza ............... B29D 11/00221 264/1.32 |
| 8,535,043 | B2 | * | 9/2013 | Perez .................... B29C 33/303 249/160 |
| 8,908,282 | B2 | * | 12/2014 | Yang ...................... G02B 7/022 359/642 |
| 9,102,110 | B2 | * | 8/2015 | Bruce ............... B29D 11/00221 |
| 2002/0140117 | A1 | * | 10/2002 | Russell ............... B29C 33/0022 264/1.36 |
| 2003/0062640 | A1 | * | 4/2003 | Ansell ................. B29C 33/3842 264/1.32 |
| 2003/0077350 | A1 | * | 4/2003 | Horner ............. B29D 11/00057 425/195 |
| 2004/0075182 | A1 | * | 4/2004 | Gobron ............... B29C 33/0088 264/2.5 |
| 2004/0099971 | A1 | * | 5/2004 | Su ..................... B29D 11/00413 264/1.32 |
| 2005/0100631 | A1 | * | 5/2005 | Baba ................. B29D 11/00057 425/406 |
| 2005/0212155 | A1 | * | 9/2005 | Matsuzawa ...... B29D 11/00125 264/1.32 |
| 2006/0071356 | A1 | * | 4/2006 | Beebe ............... B29D 11/00057 264/2.2 |
| 2006/0103037 | A1 | * | 5/2006 | Su ..................... B29D 11/00413 264/1.7 |
| 2006/0145372 | A1 | * | 7/2006 | Jones .................. B29C 45/2673 264/1.32 |
| 2006/0202367 | A1 | * | 9/2006 | Knutzen .......... B29D 11/00221 264/1.32 |
| 2007/0109493 | A1 | * | 5/2007 | Clerc ................. B29C 45/14073 351/159.01 |
| 2007/0210466 | A1 | * | 9/2007 | Saeki .................... B29C 43/361 264/1.32 |
| 2007/0212438 | A1 | * | 9/2007 | Saeki .................... B29C 43/021 425/408 |
| 2009/0051059 | A1 | | 2/2009 | Widman et al. |
| 2009/0053351 | A1 | | 2/2009 | Widman et al. |
| 2010/0047380 | A1 | | 2/2010 | Widman et al. |

FOREIGN PATENT DOCUMENTS

| | | |
|---|---|---|
| JP | 2007-212771 | 8/2007 |
| WO | WO 9710527 | 3/1997 |
| WO | WO 2005/005121 A2 | 1/2005 |
| WO | WO 2005/050289 A1 | 6/2005 |
| WO | WO 2008039485 A1 | 4/2008 |
| WO | WO 2009/025845 A1 | 2/2009 |
| WO | WO 2009/025848 A2 | 2/2009 |
| WO | WO 2010 /088266 A1 | 8/2010 |

OTHER PUBLICATIONS

International Search Report for corresponding Application No. PCTUS2013048572 date of mailing Oct. 28, 2013.

* cited by examiner

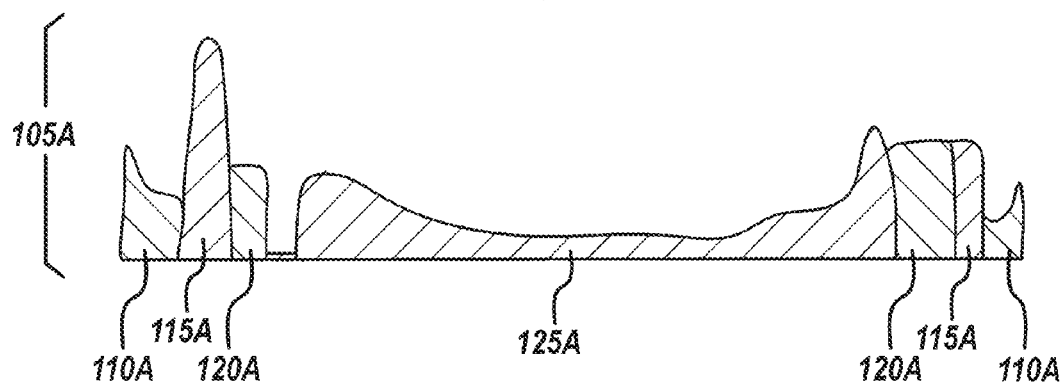
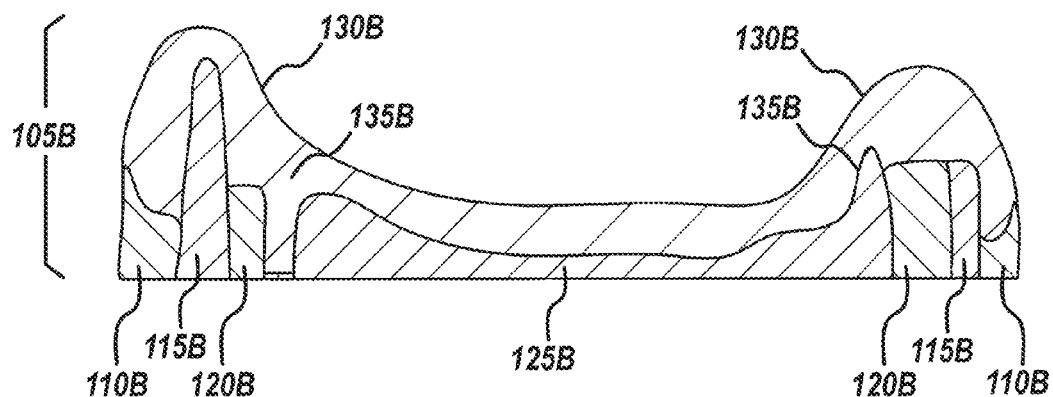
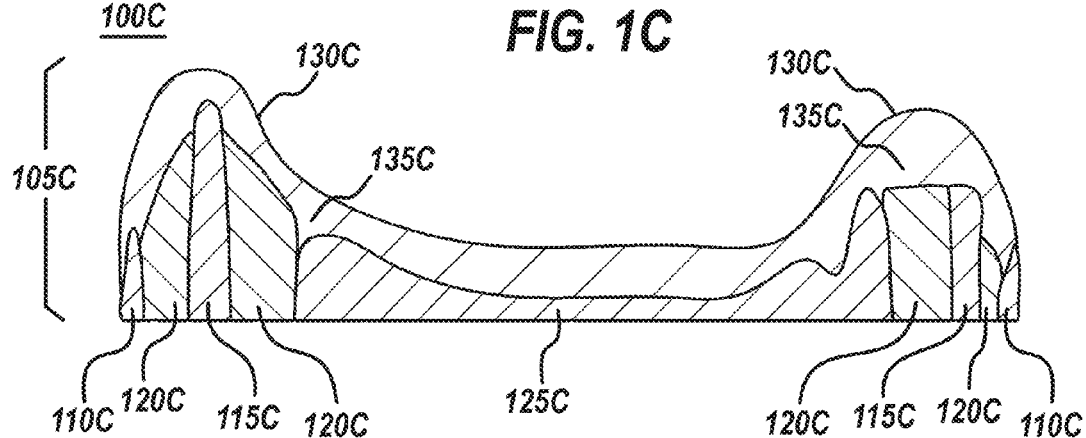

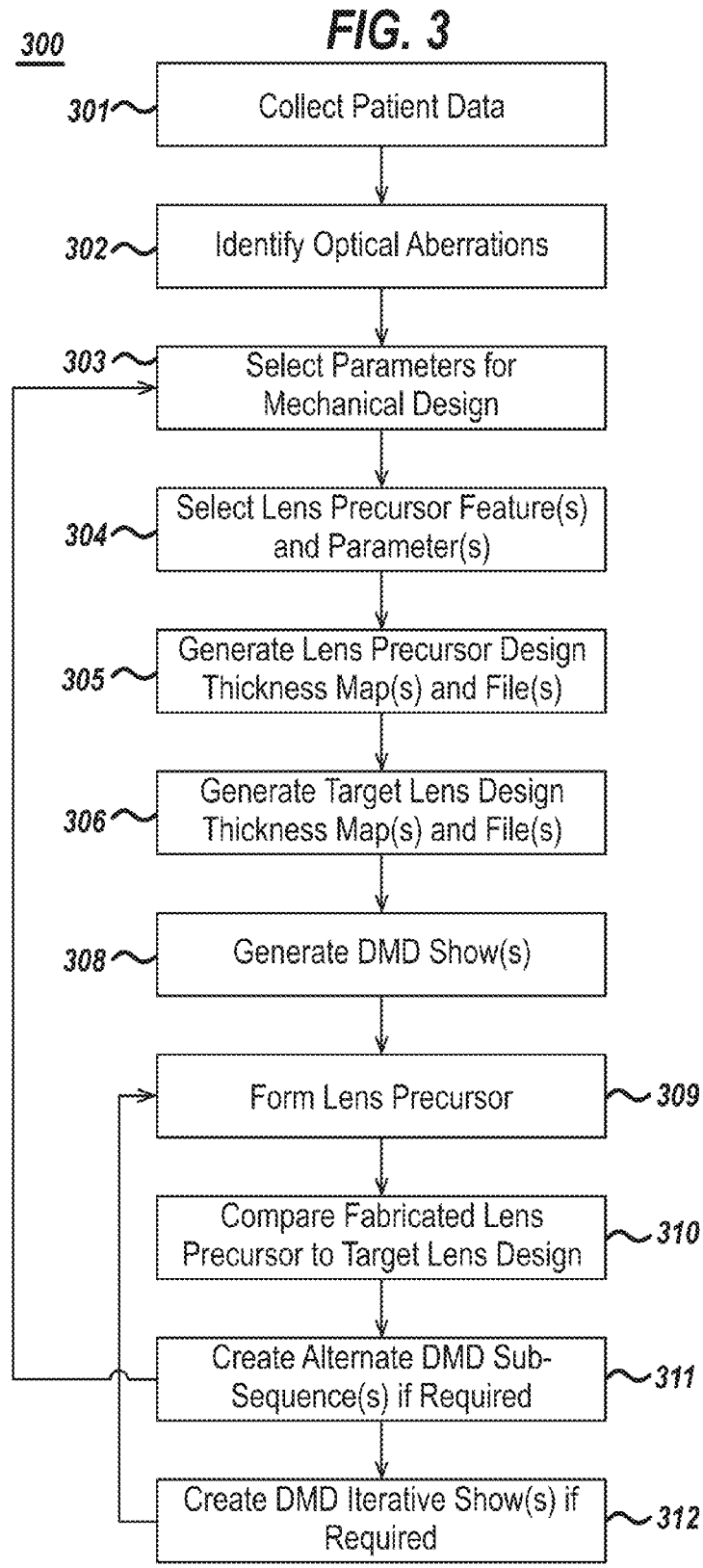

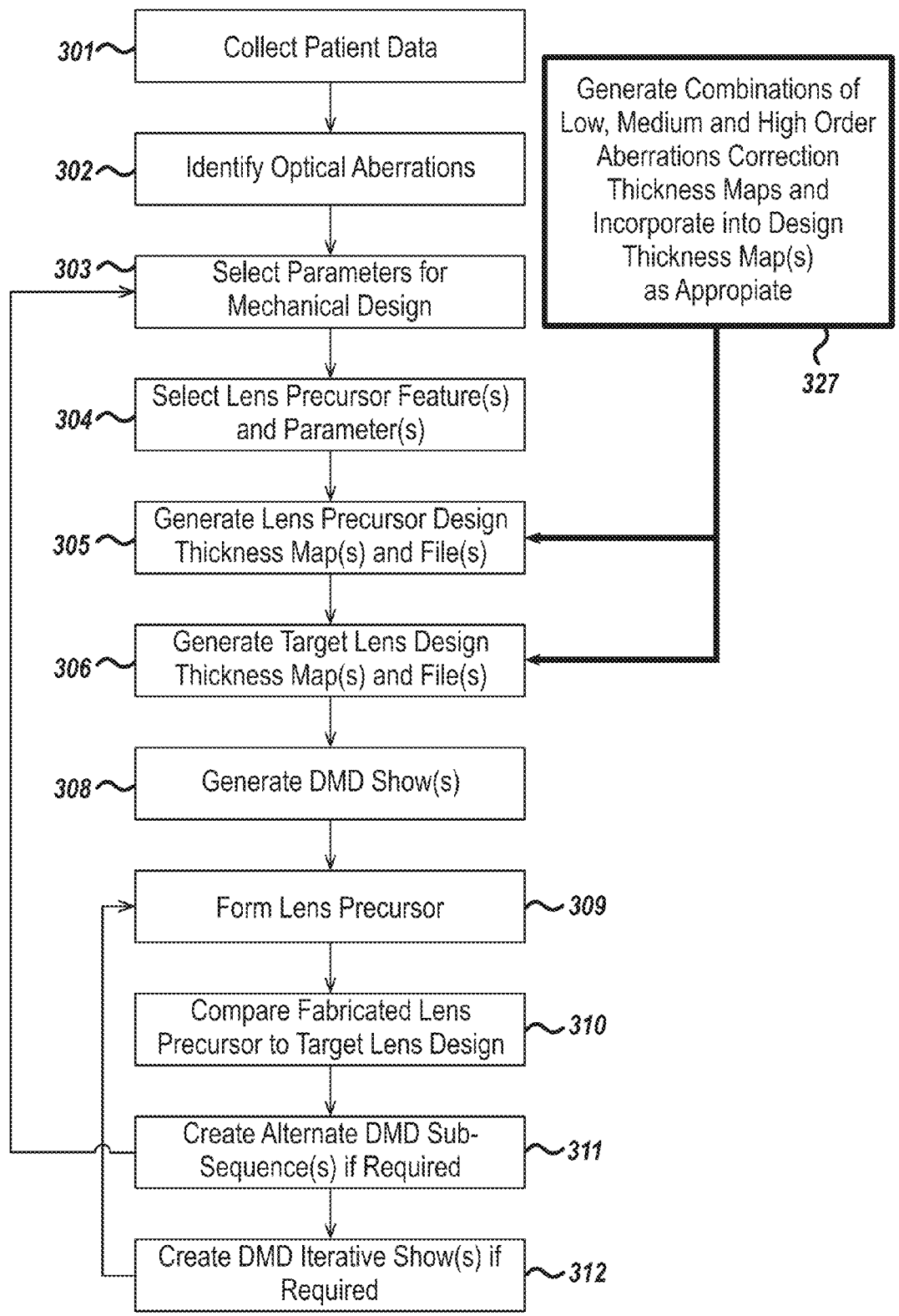

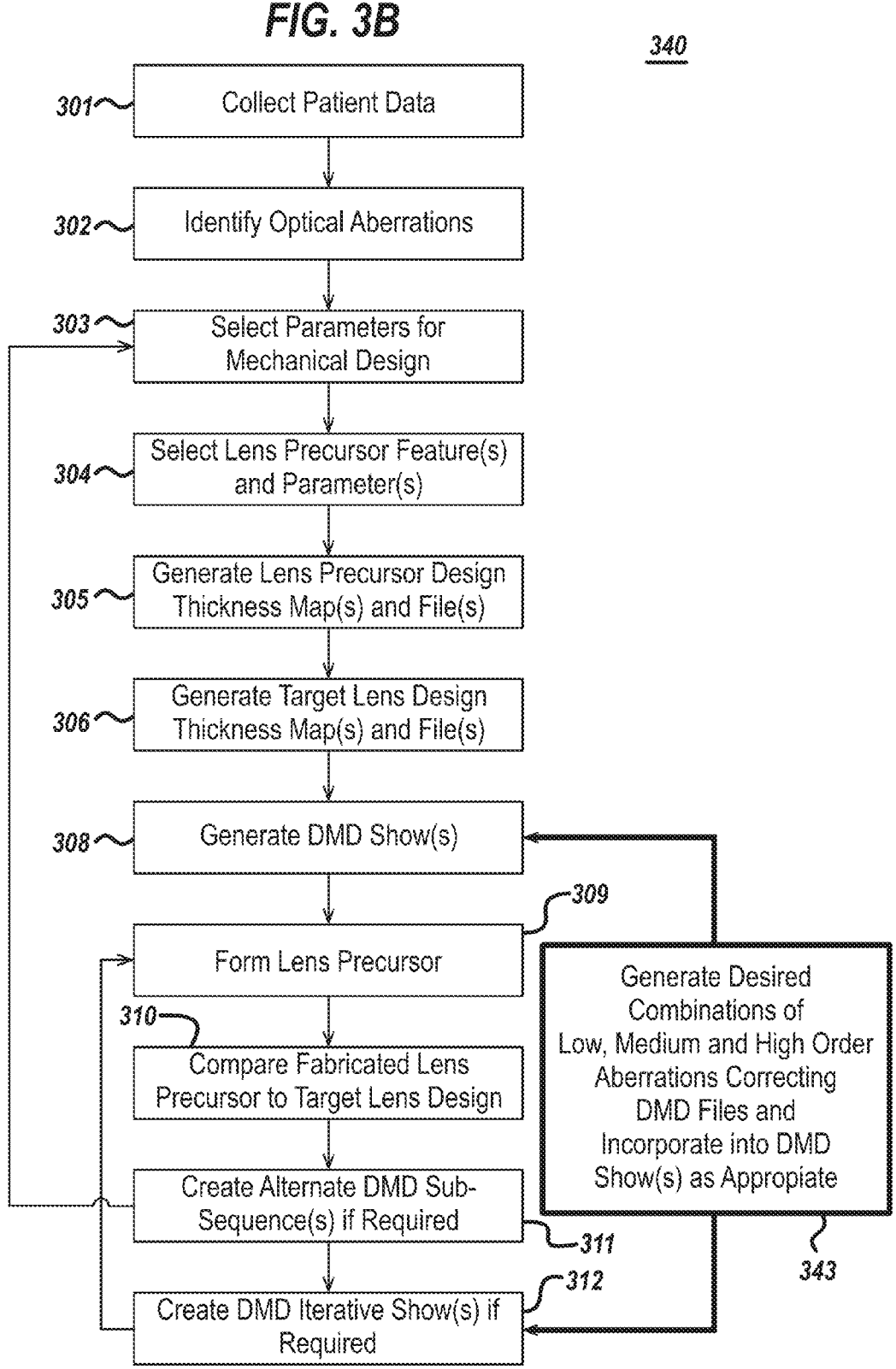

Header Info:
...
...
...
---------------- data format (y, x, th {mm}) ----------
----------
...
...
...

| | | |
|---|---|---|
| 1.646100 | 2.259900 | 0.139302 |
| 1.646100 | 2.273850 | 0.139522 |
| 1.646100 | 2.287800 | 0.139745 |
| 1.646100 | 2.301750 | 0.139969 |
| 1.646100 | 2.315700 | 0.140194 |
| 1.646100 | 2.329650 | 0.140422 |
| 1.646100 | 2.343600 | 0.140651 |
| 1.646100 | 2.357550 | 0.140882 |
| 1.646100 | 2.371500 | 0.141114 |
| 1.646100 | 2.385450 | 0.141348 |
| 1.646100 | 2.399400 | 0.141584 |
| 1.646100 | 2.413350 | 0.141822 |
| 1.646100 | 2.427300 | 0.142061 |
| 1.646100 | 2.441250 | 0.142302 |
| 1.646100 | 2.455200 | 0.142545 |
| 1.646100 | 2.469150 | 0.142790 |
| 1.646100 | 2.483100 | 0.143036 |
| 1.646100 | 2.497050 | 0.143284 |
| 1.646100 | 2.511000 | 0.143534 |
| 1.646100 | 2.524950 | 0.143786 |
| 1.646100 | 2.538900 | 0.144040 |
| 1.646100 | 2.552850 | 0.144295 |
| 1.646100 | 2.566800 | 0.144553 |
| 1.646100 | 2.580750 | 0.144812 |
| 1.646100 | 2.594700 | 0.145073 |
| 1.646100 | 2.608650 | 0.145336 |
| 1.646100 | 2.622600 | 0.145600 |
| 1.646100 | 2.636550 | 0.145867 |
| 1.646100 | 2.650500 | 0.146136 |
| 1.646100 | 2.664450 | 0.146406 |

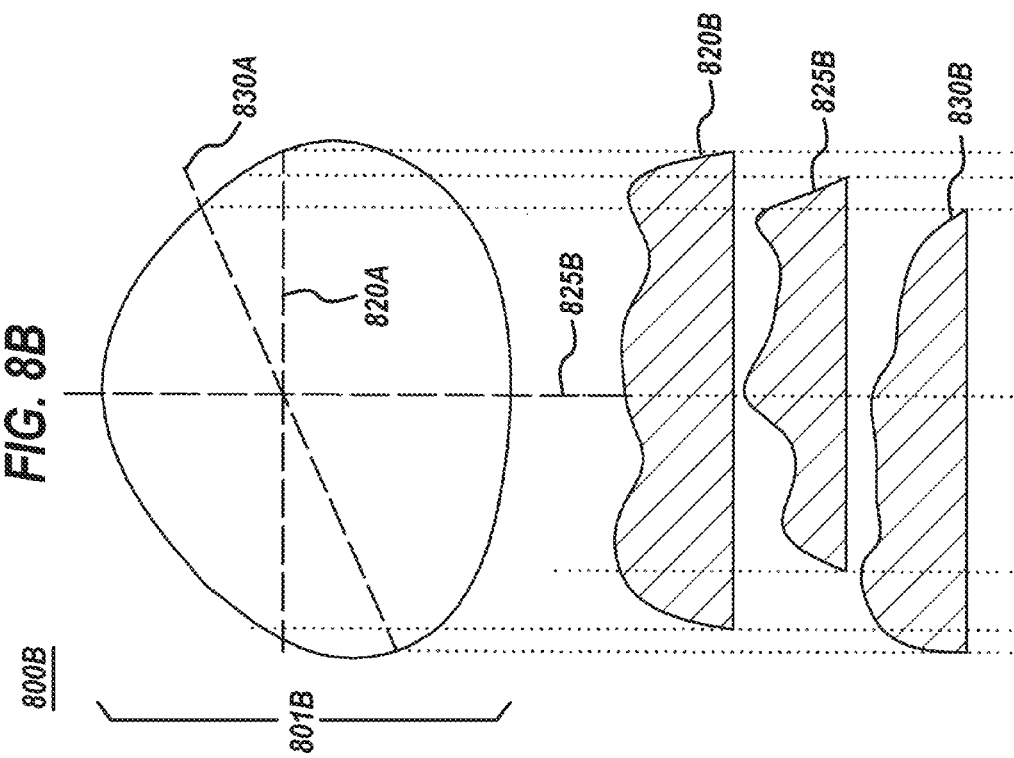
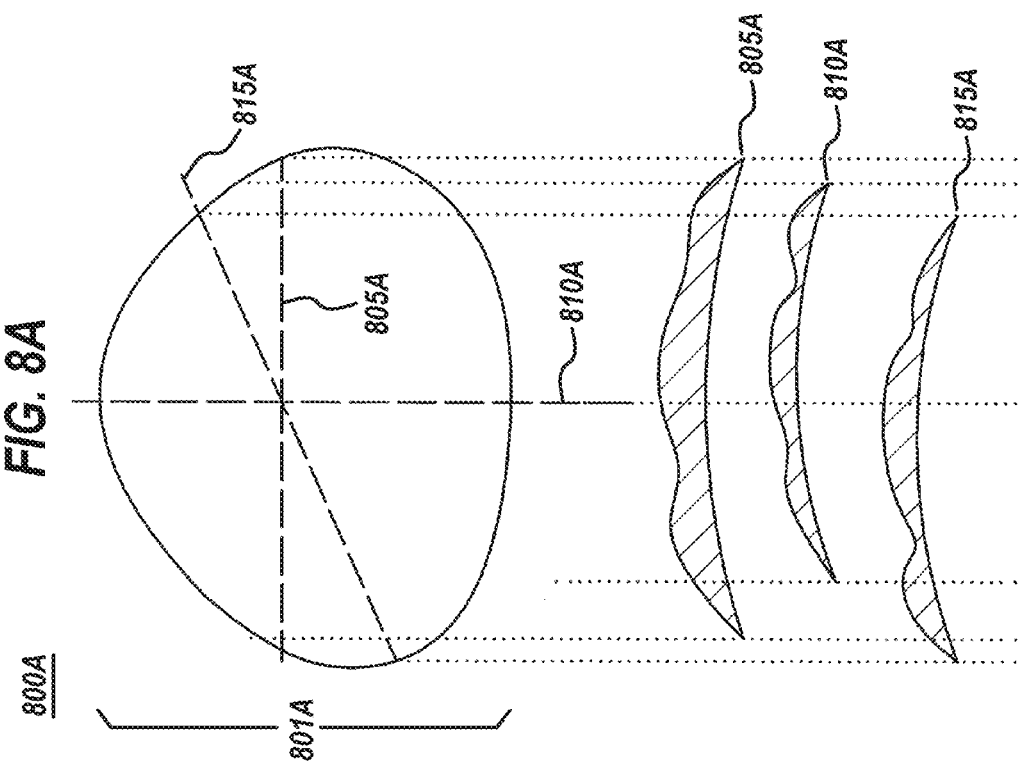

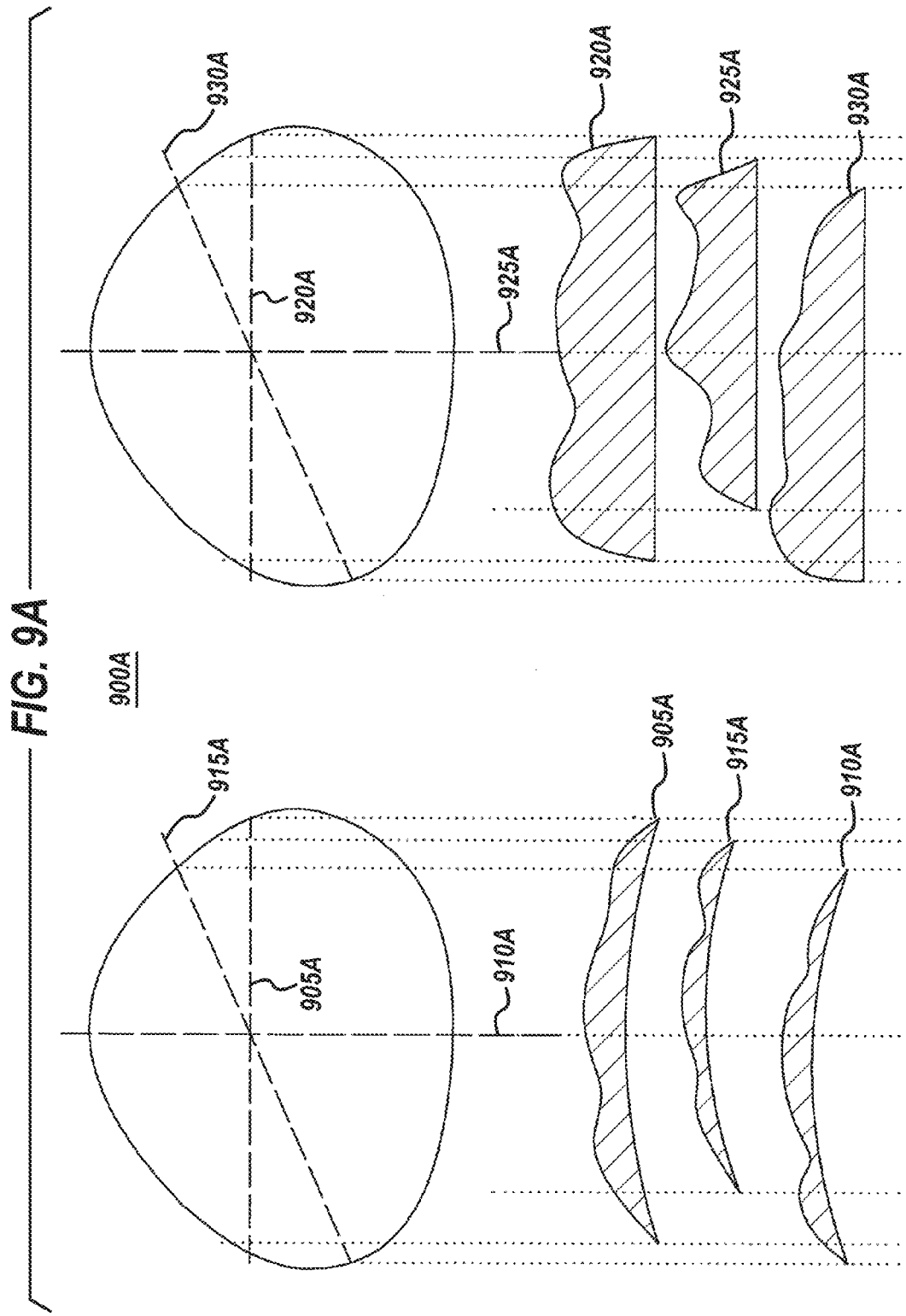

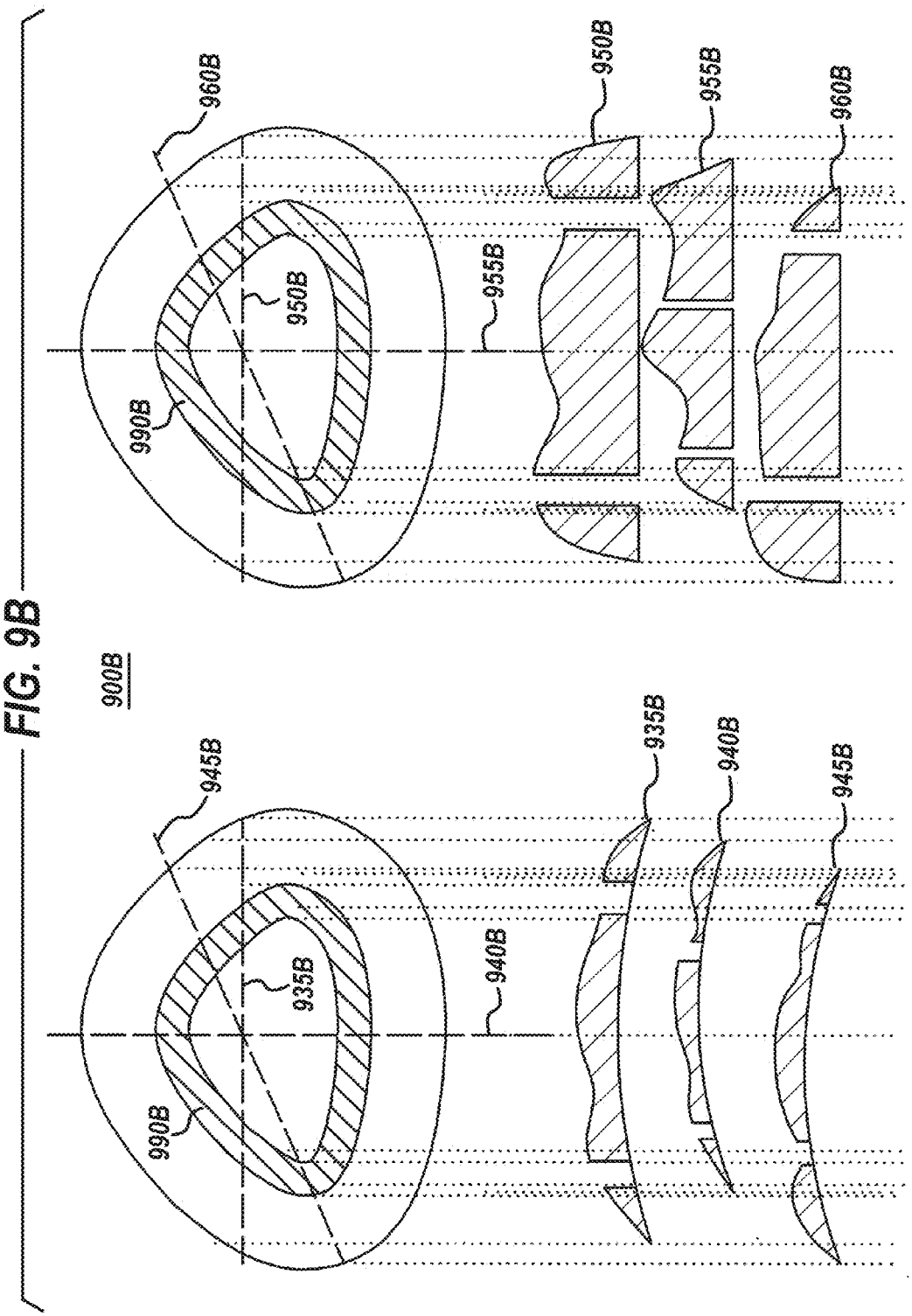

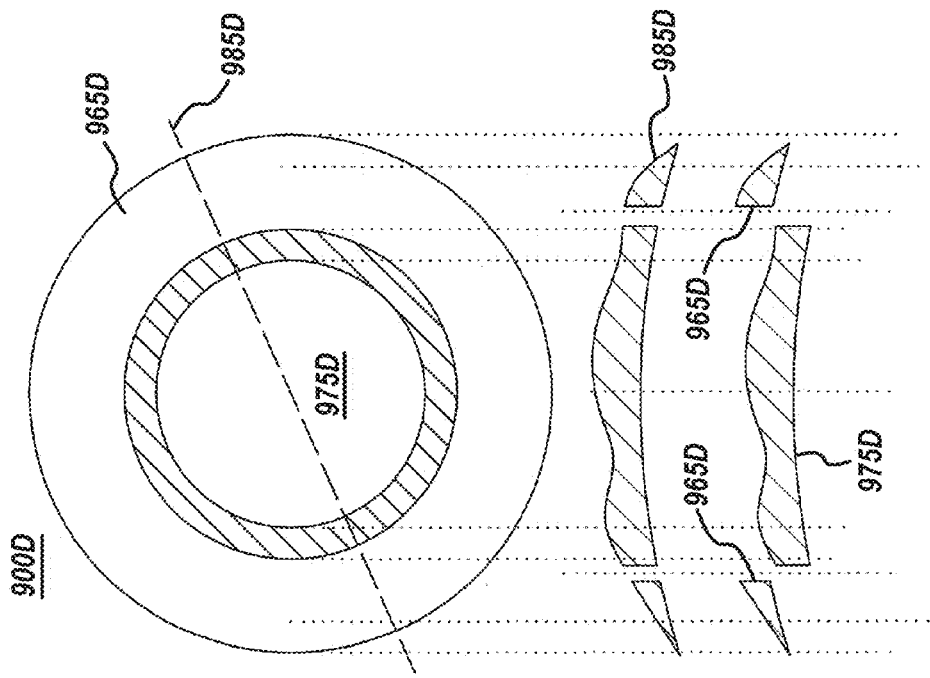
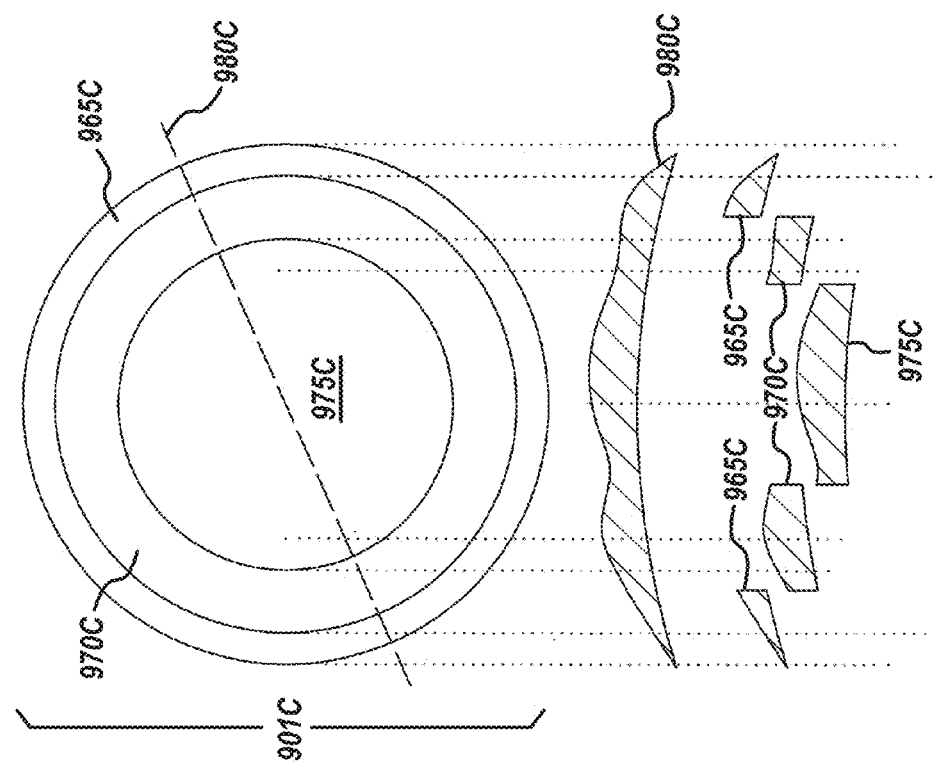

Header Info:
...
...
...
-------------------- data format (y, x, th {mm}) --------------------
...
...
...
1.646100     2.259900     0.119792
1.646100     2.273850     0.120146
1.646100     2.287800     0.120499
1.646100     2.301750     0.120848
1.646100     2.315700     0.121217
1.646100     2.329650     0.121592
1.646100     2.343600     0.121949
1.646100     2.357550     0.122293
1.646100     2.371500     0.122624
1.646100     2.385450     0.122931
1.646100     2.399400     0.123210
1.646100     2.413350     0.123458
1.646100     2.427300     0.123646
1.646100     2.441250     0.123782
1.646100     2.455200     0.123917
1.646100     2.469150     0.123997
1.646100     2.483100     0.124029
1.646100     2.497050     0.124046
1.646100     2.511000     0.124038
1.646100     2.524950     0.123924
1.646100     2.538900     0.123792
1.646100     2.552850     0.123664
1.646100     2.566800     0.123502
1.646100     2.580750     0.123311
1.646100     2.594700     0.123121
1.646100     2.608650     0.122917
1.646100     2.622600     0.122685
1.646100     2.636550     0.122410
1.646100     2.650500     0.122075
1.646100     2.664450     0.121675
...
...
...

FIG. 10

LENS PRECURSOR WITH FEATURES FOR THE FABRICATION OF AN OPHTHALMIC LENS

CROSS REFERENCE TO RELATED APPLICATIONS

This application is the national stage of PCT Application No. PCT/US2013/048572 filed Jun. 28, 2013, which claims priority from U.S. Provisional Application No. 61/665,973, Filed Jun. 29, 2012; the entire disclosures of which are hereby incorporated in their entirety.

FIELD OF USE

This invention describes a lens precursor device with one or more lens precursor features that may be useful in the fabrication of an ophthalmic lens. More specifically, the lens precursor is a composite object comprising a lens precursor form and fluent lens reactive media in contact with a lens precursor form, and said lens precursor may be useful in the fabrication of ophthalmic lenses in a free-form manner.

BACKGROUND OF THE INVENTION

Currently, ophthalmic lenses are often made by cast molding, in which a reactive monomer material is deposited in a cavity defined between optical surfaces of opposing mold parts. To prepare a lens using such mold parts, an uncured hydrogel lens formulation is placed between a plastic disposable front curve mold part and a plastic disposable back curve mold part.

The front curve mold part and the back curve mold part are typically formed via injection molding techniques wherein melted plastic is forced into highly machined steel tooling with at least one surface of optical quality.

The front curve and back curve mold parts are brought together to shape the Lens according to desired lens parameters. The lens formulation is subsequently cured, for example by exposure to heat and light, thereby forming a lens. Following cure, the mold parts are separated and the lens is removed from the mold parts for hydration and packaging. However, the nature of cast molding processes and equipment make it difficult to form custom lenses specific to a particular patient's eye or a particular application.

Consequently, in prior descriptions by the same inventive entity, methods and apparatus for forming customized lenses via the use of free-form techniques have been described. An important aspect of these novel techniques is that a lens is produced in a free-form manner, that is where one of two lens surfaces is formed in a free-formed manner without the need of using cast molding, lathing, or other tooling.

A free-formed surface and base may include fluent lens s reactive media included in the free-formed surface at some point during the formation. This combination results in a device sometimes referred to as a lens precursor. Fixing radiation and hydration treatments may typically be utilized to convert a lens precursor into an ophthalmic lens.

Some of the free-formed lenses created in this manner may need different methods and/or structural features for the control of all or some of the fluent lens reactive media included in the lens precursor. By controlling some of all of the fluent lens reactive media, physical and/or optical parameters of a lens design may be produced. The new methods and features are the subject matter of the present invention.

SUMMARY OF THE INVENTION

The present invention is directed to a lens precursor and methods of forming said lens precursor, for the fabrication of an ophthalmic lens. More specifically, the lens precursor which may comprise one or more lens precursor features used as part of a substructure for at least portions of a fluent lens reactive media portion of the lens precursor.

Some aspects of the present invention include different methods and apparatus for iteration, for example, for the creation of a DMD show and DMD file, for fabricating a lens precursor that may comprise one or more lens precursor features. Generally, applicable patient data and product data may be collected and utilized to produce standard or custom product designs. A desired product design or lens precursor design may comprise one or both of lens precursor features and fluent lens reactive media surfaces.

Lens designs, for a desired product may be generated from lens precursor designs, thickness maps and associated files. Separate thickness maps and associated files may be used as stand-alone files, or combined with other thickness maps. For example, DMD shows may be generated from lens precursor thickness maps and associated files, lens design thickness maps and associated files, DMD subsequence(s) or other methods, and utilized in fabrication of a lens precursor.

Fabricated lens precursors may be compared to thickness maps and associated files to determine conformance to desired product designs. In cases where a fabricated product may not or does not conform to desired requirements, DMD Iterative shows may be created and modified in order to fabricate a lens precursor that may be closer to a desired product design.

The following is a non-exhaustive list of exemplary embodiments of the invention that are or may be claimed.

Embodiment 1

An ophthalmic lens precursor comprising:

a lens precursor form comprising a crosslinkable media comprising a photoabsorptive component;

a first surface and a second surface, wherein the first surface comprises a portion of a first crosslink density degree at least partially polymerized at or above a gel point;

a fluid second surface comprising a second crosslink density degree of cure less than the gel point; and wherein the first surface includes at least partially polymerized topological features that may act as a lens precursor form substructure and at least a portion of said second surface may be incorporated into an ophthalmic lens.

Embodiment 2

The ophthalmic lens precursor of Embodiment 1, wherein the topological features include one or more of a lens edge feature, a bump feature, a drain channel feature, a volumator feature, a lake feature, and a stabilization zone feature.

Embodiment 3

The ophthalmic lens precursor of Embodiment 2, further comprising more than one of each one or more said topological feature(s) included.

Embodiment 4

The ophthalmic lens precursor of Embodiment 2, wherein each included feature comprises one or more of a specified height, length, shape and width.

Embodiment 5

The ophthalmic lens precursor of Embodiment 4, wherein the angular width of one or more of said included features may be continuous throughout 360 degrees of the lens precursor.

Embodiment 6

The ophthalmic lens precursor of Embodiment 4, wherein the angular width of one or more of said included features is non-continuous and generally present in discrete portions of said first surface.

Embodiment 7

The ophthalmic lens precursor of Embodiment 1, wherein said first surface further comprises a moat feature in one or more discrete portions.

Embodiment 8

The ophthalmic lens precursor of Embodiment 1, additionally comprising marks in one or both of said first surface and fluid second surface.

Embodiment 9

The ophthalmic lens precursor of Embodiment 1, wherein at least a portion may be rotationally symmetrical.

Embodiment 10

The ophthalmic lens precursor of Embodiment 1, wherein the shape of the lens precursor may generally be circular.

Embodiment 11

The ophthalmic lens precursor of Embodiment 1, wherein the shape of the lens precursor may generally be oval shaped.

Embodiment 12

The ophthalmic lens precursor of Embodiment 2, wherein one or more of said features included may be described mathematically by one or more of height, width, length, shape, and location of the feature.

Embodiment 13

The ophthalmic lens precursor of Embodiment 2, wherein one or more of said features included may be obtained empirically from one or more designs of lens precursor (s) or portions thereof.

Embodiment 14

The ophthalmic lens precursor of Embodiment 1, wherein said lens precursor may be further processed into an ophthalmic lens.

Embodiment 15

The ophthalmic lens precursor of Embodiment 14, wherein the processing comprises stabilization of at least a portion of the second fluid surface.

Embodiment 16

The ophthalmic lens precursor of Embodiment 14, wherein the processing further comprises fixing at least a portion of the second fluid surface using actinic radiation to a crosslink density degree at least partially polymerized at or above a gel point.

Embodiment 17

The ophthalmic lens precursor of Embodiment 3, wherein more than one bump features are used for the formation of at least a portion of a bifocal lens.

Embodiment 18

The ophthalmic lens precursor of Embodiment 3, wherein more than one bump features are used for the formation of at least a portion of a trifocal lens.

Embodiment 19

The ophthalmic lens precursor of Embodiment 3, wherein more than one bump features are used for the formation of at least a portion of a lenslet array.

Embodiment 20

The ophthalmic lens precursor of Embodiment 1, wherein the lens precursor is formed in a free-form manner.

Embodiment 21

The ophthalmic lens precursor of Embodiment 20, wherein the free form manner includes voxel by voxel free forming methods.

Embodiment 22

An ophthalmic lens precursor comprising:
a lens precursor form comprising a crosslinkable media comprising a photoabsorptive component;
a first surface and a second surface, wherein the first surface comprises a portion of a first crosslink density degree at least partially polymerized at or above a gel point;
a fluid second surface comprising a second crosslink density degree of cure less than the gel point; and
wherein the first surface includes at least partially polymerized topological features that may be used to determine the optical magnification of apparatus used to incorporate the lens precursor into an ophthalmic lens.

Embodiment 23

The ophthalmic lens precursor of Embodiment 22, wherein the topological features include one or more of; a lens edge feature, a bump feature, a drain channel feature, a volumator feature, a lake feature, and a stabilization zone feature.

Embodiment 24

The ophthalmic lens precursor of Embodiment 22, further comprising one or more marks.

Embodiment 25

The ophthalmic lens precursor of Embodiment 22, wherein the one or more marks can be embedded into one or more of the topological features.

Embodiment 26

The ophthalmic lens precursor of Embodiment 22, wherein the one or more Marks can be on the one or more of the topological features.

Embodiment 27

An ophthalmic lens precursor comprising:
a lens precursor form comprising a crosslinkable media comprising a photoabsorptive component;
a first surface and a second surface, wherein the first surface comprises a portion of a first crosslink density degree at least partially polymerized at or above a gel point;
a fluid second surface comprising a second crosslink density degree of cure less than the gel point; and
wherein the first surface includes at least partially polymerized topological features that can be used to align the lens precursor with one or more part of an apparatus used to incorporate the lens precursor into an ophthalmic Lens.

Embodiment 28

The ophthalmic lens precursor of Embodiment 27, wherein the topological features include one or more of a lens edge feature, a bump feature, a drain channel feature, a volumator feature, a lake feature, and a stabilization zone feature.

Embodiment 29

The ophthalmic lens precursor of Embodiment 27, further comprising one or more marks.

Embodiment 30

The ophthalmic lens precursor of Embodiment 27, wherein the one or more marks can be embedded into one or more of the topological features.

Embodiment 31

The ophthalmic lens precursor of Embodiment 27, wherein the one or more marks may be on the one or more of the topological features.

Embodiment 32

An ophthalmic lens precursor comprising:
a lens precursor form comprising a crosslinkable media comprising a photoabsorptive component;
a first surface and a second surface, wherein the first surface comprises a portion of a first crosslink density degree at least partially polymerized at or above a gel point;
a fluid second surface comprising a second crosslink density degree of cure less than the gel point; and
wherein the first surface includes at least partially polymerized topological features that may be used as lens identifiers upon incorporating the lens precursor into an ophthalmic lens.

Embodiment 33

The ophthalmic lens precursor of Embodiment 32, wherein the lens identifiers are used as anti-counterfeiting marks.

BRIEF DESCRIPTION OF THE DRAWINGS

The foregoing and other features and advantages of the invention will be apparent from the following, more particular description of preferred embodiments of the invention, as illustrated in the accompanying drawings.

FIG. 1A illustrates an exemplary side view cross-sectional representation of a lens precursor form in flat space.

FIG. 1B illustrates an exemplary side view cross-sectional representation of a lens precursor that comprises single lens precursor features of multiple types in flat space.

FIG. 1C illustrates an exemplary side view cross-sectional representation of a lens precursor that comprises single and multiple types of lens precursor features in flat space.

FIG. 3 illustrates exemplary method steps that may be used to implement some embodiments of the present invention.

FIG. 3A illustrates additional method steps that may also be used to implement some embodiments of the present invention.

FIG. 3B illustrates yet additional method steps that may also be used to implement some embodiments of the present invention.

FIG. 5 illustrates sample data generated by software program(s) representing a portion of a thickness map.

FIG. 8A illustrates an exemplary top view and cross-sectional representations of a Lens precursor in Curved Space.

FIG. 8B illustrates an exemplary top view and side view cross-sectional representations of a lens precursor in flat space, depicting exaggerated thickness profiles.

FIG. 9A illustrates an exemplary representation of a continuous surface single part design in top and side cross sectional views, in both flat and curved space.

FIG. 9B illustrates an exemplary representation of a non-continuous surface single part design in top and side cross sectional views, in both flat and curved space.

FIG. 9C illustrates an exemplary representation of a continuous surface multi-part design in top and side cross sectional views in curved space.

FIG. 9D illustrates an exemplary representation of a non-continuous surface multi-part design in top and side cross sectional views in curved space.

FIG. 10 illustrates sample data generated by software program(s) representing a portion of a DMD file.

DETAILED DESCRIPTION OF THE INVENTION

Figure 1D:
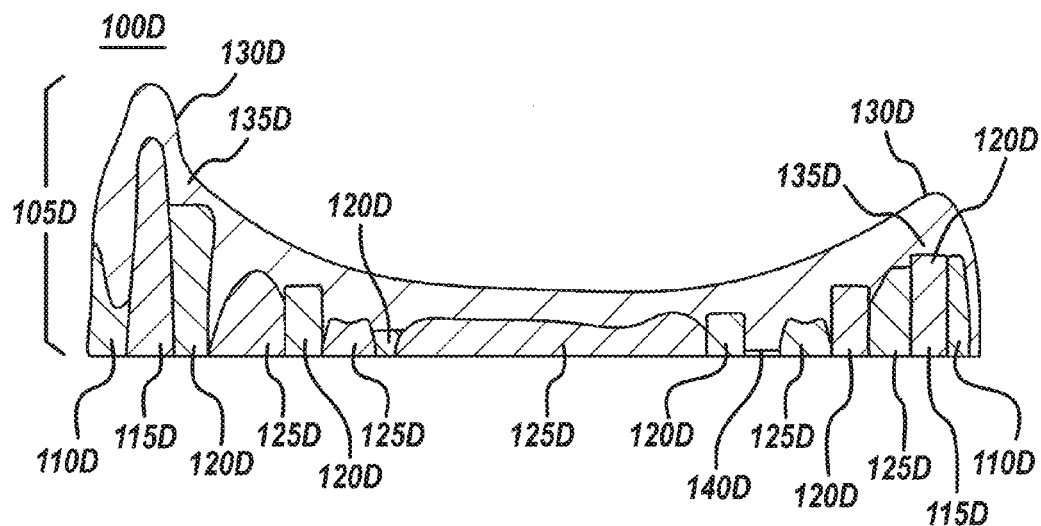
FIG. 1D illustrates an exemplary side view cross-sectional representation of a lens precursor that comprises single and multiple types of lens precursor features, in addition to a moat feature in flat space.

The present invention provides for a lens precursor used to fabricate ophthalmic lenses, said lens precursor device which may comprise an array of topological features used to create a substructure that may control properties/characteristics of a final ophthalmic lens. In the following sections, detailed descriptions of exemplary embodiments of the invention are given. The description of both preferred and alternate embodiments though detailed are exemplary embodiments only, and it is understood to those skilled in the art that variations, modifications, and alterations may be apparent. It is therefore to be understood that said exemplary embodiments do not limit the broadness of the aspects of the underlying invention. Method steps described herein are listed in a logical sequence in this discussion; however, this sequence in no way limits the order in which they may be implemented unless specifically stated.

GLOSSARY

In the description directed to the presented invention, various terms may be used for which the following definitions will apply:

"Acceptance Criteria" as used herein, refers to specified parameter ranges and threshold values in the system that can be correlated to measured parameters and values of a fabricated ophthalmic lens, lens precursor form or lens precursor, to determine if the product is acceptable for its intended purpose.

"Bump(s) features" as used herein, refer to lens precursor protrusions of cured reactive media, which have been cured at or above a gel point, thereby creating topological features. Bumps may be formed, for example, by reducing the actinic radiation exposure in one or more voxel location(s) by decreasing the exposure signal given in a DMD instruction(s) at these locations. In an analogous manner, bumps may also be formed by increasing the actinic radiation exposure in one or more voxel location(s) by increasing the exposure signal given in a DMD instruction(s) at these locations. Bumps may be located in all of or portions of the optical zone to assist in the formation of one or more lenslet arrays upon curing in discrete portions therein. Alternately or additionally, bumps may be formed in predetermined areas of the optical zone for the formation of a bifocal lens.

"Catalog Item" as used herein, refers to a file, feature, component, design, data, or descriptor that may be temporarily or permanently stored, such as in libraries or databases, and can be recalled for use.

"Curved Space" as used herein, refers to a coordinate mapping space (e.g., Cartesian, polar, spherical, etc.) where the curvature of a design has not been removed. As an exemplary illustration of such, an ophthalmic lens may be formed upon a back curve mold piece. This lens when inspected may have a three dimensional shape fundamentally related to the three dimensional shape of the mold piece. When cross sections are depicted for this example lens in curved space the bottom of these cross sections will be curved in a manner similar to the curve of the mold piece. For better resolution of the lens front surface shape, in some treatments of cross sectional depictions, the thickness of the material above the back curve surface may be magnified. In these cases, the cross section may still be described as being presented in curved space.

"Custom Product" as used herein, refers to a product including one or more parameters that may be available in other than customary or standard products and/or settings. Custom product parameters can allow for more precisely targeted sphere power, cylinder power, and cylinder axis (e.g., −3.125D/−0.47D×18°) than standard products. The customized settings may also relate to base curves, diameters, stabilization profiles, and thickness profiles based upon a particular product offering and the intended use of the product.

"Digital Core Break" as used herein, refers to a range of products where select subsets of lens precursor features or control parameters are kept identical. For example, in a lens "digital core break" family offered with different power and sphere ranges, the lens edge, stabilization zone features and volumator features may be identical for all low power correction ranges.

"DMD control software" as used herein, refers to software that organizes and utilizes DMD files and DMD shows as desired. For example, the software may be used to enable fabrication or post processing of lens precursors comprising lens precursor features.

"DMD File" as used herein, refers to a collection of instructional data points that may be used to activate mirrors on a DMD, and thereby at least partially enable a lens or lens precursor or lens precursor form or lens precursor feature(s) to be fabricated. A DMD file can have various formats, with (x, y, th), and (r, θ, th) being the most common where, for example "x" and "y" are Cartesian coordinate locations of DMD mirrors, "r" and "θ" are polar coordinate locations of DMD mirrors, and "th" represents thickness instructions controlling DMD mirror states. DMD files may comprise data on a regularly or irregularly spaced grid.

"DMD Iterative Show" as used herein, refers to a collection of time based instructional data points that may be used to control activation of mirrors on a DMD, and enable a lens, lens precursor, lens precursor form, or lens precursor feature(s) to be fabricated. A DMD iteration show may be used to fabricate a lens, lens precursor, or lens precursor feature(s) that may be closer to a design target than a lens, lens precursor, or lens precursor feature(s) fabricated by a preceding DMD show and/or a DMD sub-sequence. DMD iteration shows may comprise data on a regularly or irregularly spaced grid.

"DMD Show" as used herein, refers to a time based sequenced series of projection patterns emanating from a DMD device onto a forming optic to fabricate a lens or lens precursor or lens precursor form or lens precursor feature(s). A DMD show may be sub-divided into a number of DMD sub-sequences. A DMD show may have various formats, with (x, y, t), and (r, θ, t) being the most common where, for example "x" and "y" are Cartesian coordinate locations of DMD mirrors, "r" and "θ" are polar coordinate locations of DMD mirrors, and "t" represents time instructions controlling DMD mirror states. DMD shows may comprise data on a regularly or irregularly spaced grid.

"DMD Sub-sequence" as used herein, refers to one or more portions of a DMD show in which one or more of the projection characteristics of the DMD show may be modified. Modifications to a sequence may include one or more of a spatial pattern, a radiant intensity level, a spectral region to project, a mirror bit-splitting arrangement, direction of a projection pattern, and a time order of a projection pattern.

"DMD" as used herein, a digital micro-mirror device is a bistable spatial light modulator comprising of an array of movable micro-mirrors functionally mounted over a CMOS SRAM. Each mirror is independently controlled by loading data into the memory cell below the mirror to steer reflected light, spatially mapping a pixel of video data to a pixel on a display. The data electrostatically controls the mirror's tilt angle in a binary fashion, where the mirror states are either +X degrees (on) or −X degrees (off). For current devices, X can be either 10 degrees or 12 degrees (nominal). Light reflected by the on mirrors then is passed through a projection lens and onto a screen. Light is reflected off to create a dark field, and defines the black-level floor for the image. Images are created by gray-scale modulation between on and off levels at a rate fast enough to be integrated by the observer. The DMD (digital micro-mirror device) is sometimes DLP projection systems.

"Drain Channel" as used herein, refers to a lens precursor topological feature that may be generated by either one or both reduced and increased exposure of voxel locations to actinic radiation by control instruction(s) in an analogous fashion to that discussed in the definition for bump features. The topological feature may be of a shape that can enable fluent lens reactive media to do one or more of the following: flow across, away from, and settle on, all or at least a portion of a polymerized lens precursor, lens precursor form, or another other lens precursor feature(s). The topographical feature may include, for example continuous or discrete segmented elongate depressions in portions of the gelled portion of the lens precursor. Drain channels may be placed side by side and configured to enable the flow of fluent lens reactive media across the lens precursor form.

"Fabrication Process Conditions" as used herein, refers to settings, conditions, methods, equipment, and processes used in fabrication of one or more of a lens precursor, a lens precursor form, and a lens.

"Flat Space" as used herein, refers to coordinate mapping space, (e.g., Cartesian, polar, spherical), where curvature of a design being considered has been removed/flattened. As an illustration of such a depiction, an example ophthalmic lens may be formed upon a back curve mold piece. This example lens when inspected may have a three dimensional shape fundamentally related to the three dimensional shape of the mold piece. When cross sections are depicted for this example lens in flat space the bottom of these cross sections may be "removed/flattened" which results in the curved back curve shape being represented by a flat line. For better resolution of the lens front surface shape, in some treatments of cross sectional depictions, the thickness of the material above the now "removed/flattened" back curve surface may be magnified. In these cases, the cross section may still be described as being presented in flat space.

"Fluent Lens Reactive Media" as used herein and sometimes referred to as "Fluent Lens reactive mixture" or "Lens forming Mixture" means a reactive mixture, prepolymer mixture or monomer mixture that is flowable in either its native form, reacted form, or partially reacted form and may be formed upon further processing into a part of an ophthalmic lens. Further, the monomer mixture or prepolymer material may be cured and crosslinked or crosslinked. Lens forming mixtures may include one or more additives such as: UV blockers, tints, photoinitiators or catalysts, and other additives one might desire in ophthalmic lenses such as, contact or intraocular lenses.

"Free-Form" and "Free-Formed" as used herein refer to a surface that is formed by crosslinking of a feactive mixture via exposure to actinic radiation on a voxel by voxel basis, with or without a fluent media layer, and is not shaped according to a cast mold, lathe, or laser ablation. Detailed description of free-form methods and apparatus are disclosed in U.S. patent application Ser. No. 12/194,981 filed Aug. 20, 2008, in U.S. patent application Ser. No. 12/195, 132 filed Aug. 20, 2008, and in EP-A-2,178,695, EP-A-2, 228,202, EP-A-2,228,201, EP-A-2,178,694 and EP-A-2, 391,500.

"High Order Optical Aberration(s)" as used herein, refers to distortion(s) in an image formed by an optical system due to optical deviations. More specifically, in an eye, it can include one or more symptoms known in the field of vision correction as spherical aberration(s), trefoil, coma, and pentafoil.

"Iterative Fabrication Process" as used herein, refers to a process of exercising an iterative loop by using one or both of DMD Iterative show(s) and modifications to fabrication process conditions in order to fabricate a lens, lens precursor form, or lens precursor that may be closer to a desired thickness map/target design than its predecessor.

"Iterative Loop" as used herein, refers to one, or a series of process steps, components and/or conditions that may enable a lens or lens precursor, lens precursor form, or lens precursor feature(s) fabrication such that each time through a loop, a lens, lens precursor, lens precursor form, or lens precursor feature(s) may be more conforming to a desired target than its predecessor.

"Lake Feature" as used herein, refers to a lens precursor topological feature that is included in some lens precursor designs. A lake feature can be generated by either one or both reduced and increased exposure of voxel locations to actinic radiation by control with DMD instruction(s) in an analogous fashion to that discussed in the definition for bump features. A lake feature sometimes referred to as a "Lake Topological feature" may include a depression in a portion of the crosslinked gelled portion of the lens precursor to contain a greater volume of fluent lens reactive media in relation to adjacent areas.

"Lens Design" as used herein, refers to form, function or both of a desired lens, which if fabricated, may provide functional characteristics comprising optical power correction, acceptable lens fit (e.g., corneal coverage and movement), and acceptable lens rotation stability. lens designs may be represented for example, in either a hydrated or un-hydrated state, in flat or curved space, in 2-dimensional or 3-dimensional space, and by a method including but not limited to, geometric drawings, power profile, shape, features, and thicknesses. Lens designs may include data associated with a regularly or irregularly spaced grid.

"Lens Edge" as used herein, refers to a topological feature capable of providing a defined edge around at least a portion of the perimeter of a lens precursor, lens precursor form, or a lens that may include fluent lens reactive media. A lens edge topological feature may be either continuous around a lens precursor or a lens, or may be present in discrete, non-continuous zones. Such a lens edge may comprises a fence structure that is configured contain a fluent lens reactive media present within the perimeter of the lens precursor form.

"Lens precursor feature," also referred to as a "feature" or a "topological feature," as used herein, refers to a non-fluent part of a substructure of a lens precursor form, which may act as an infrastructure for a lens precursor. Lens precursor features may be defined empirically or described mathematically by control parameters including height, angular width, length, shape and location. features may be generated via DMD show instructions using controlled vectors of actinic radiation and may be incorporated into an ophthalmic lens upon further processing. Examples of lens precursor features may comprise one or more of: a lens edge, a stabilization zone feature, a volumator feature, an optic zone, a moat feature, a drain channel feature, a lake feature, and bump feature.

"Lens precursor Form" as used herein, refers to a non-fluent object with at least one optical quality surface, which may be consistent with being incorporated upon further processing into an ophthalmic lens.

"Lens precursor" as used herein, means a composite object comprising of a lens precursor form and fluent lens reactive media in contact with a lens precursor form that may be rotationally symmetrical or non-rotationally symmetrical. For example, fluent lens reactive media may be formed in the course of producing a lens precursor form within a volume of reactive mixture. Separating a lens precursor form and fluent lens reactive media from a volume of reactive mixture used to produce a lens precursor form may generate a lens precursor. Additionally, a lens precursor may be converted to a different entity by either the removal of an amount of fluent lens reactive media or the conversion of an amount of fluent lens reactive media into non-fluent incorporated material.

"Lens" as used herein, refers to any ophthalmic device that resides in or on the eye. These devices may provide optical correction or may be cosmetic. For example, the term lens may refer to a contact lens, intraocular lens, overlay lens, ocular insert, optical insert or other similar device through which vision is corrected or modified, or through which eye physiology is cosmetically enhanced (e.g., iris color) without impeding vision. Lenses of the invention may be soft contact lenses made from silicone elastomers or hydrogels, which include but are not limited to silicone hydrogels, and fluorohydrogels.

"Low Order Optical Aberration(s)" as used herein, refers to a distortion(s) in an image formed by an optical system due to optical deviations. More specifically, in an eye, it may include correcting one or more symptoms known in the field of vision correction by adjusting one or more of sphere power, cylinder power, and cylinder axis.

"Minimal Energy Surface" as used herein and sometimes referred to as "MES", refers to a surface created by fluent lens reactive media formed over lens precursor features, which may be in a minimum energy state. Minimal energy surfaces may be smooth and continuous surfaces or smooth discrete segments of lens precursor features.

"Moat" as used herein, refers to a lens precursor topological feature that may be formed using fixed values in DMD show in one or more areas and is lower in height than surrounding features. Except that the feature may be defined by using fixed values in the DMD show, the general procedure for forming a moat or "Moat feature" may be performed in an analogous fashion to that described in the definition for Bump features. Additionally, a moat may be extended into or be a part of another feature, such as, a volumator. The "Moat" may be defined by a substantially discontinuous reduction in height of the lens precursor form and/or defined by a region of the lens precursor form of substantially zero or zero thickness.

"Multi-Part Design" as used herein, refers to a design where required information to reconstruct a desired profile is included in two or more files. Additionally, the two or more files may include one or more discrete, non-contiguous and non-continuous surfaces. Multi-part designs may include feature separation in an (x-y) plane which in a flat space depiction of an exemplary lens cross section may be a plane that "heads into the paper," and may also include separation in an (x-z) plane which in a similar flat space depiction of an exemplary lens cross section may be represented by the plane of the paper itself.

"Optic Zone" as used herein, refers to the region of the lens or lens precursor in which a wearer of the lens sees after the lens is formed.

"Optical Aberration" as used herein, refers to a distortion in an image formed by an optical system that may include either one or both of low order optical aberrations and high order optical aberrations.

"Product" as used herein, refers to a desired lens or lens precursor. The product may be either a "standard product" or a "custom product".

"Single Part Design" as used herein, refers to a design where required information of a desired profile may be represented in one file. Single part designs may result in a lens precursor form, which may have either a continuous surface, or a non-continuous surface.

"Stabilization Zone" as used herein, refers to a topographical feature that assists in keeping non-rotationally symmetric contact lenses correctly oriented on an eye and may be found inboard of an edge feature and outboard of one or both of an optical-power region and an optic zone.

"Standard Product" as used herein, refers to a product with limited product parameter availability, such as those currently offered with specified settings that vary in discrete steps. For example, standard products could define a family of products where sphere power parameters may only be available in 0.25D steps (e.g., −3.00D, 3.25D, −3.50D, etc.); cylinder power parameters may only be available in 0.50D steps (e.g., −0.75D, −1.25D, −1.75D, etc.); and cylinder axis parameters may only be available in 10° steps (e.g., 10°, 20°, 30°, etc.). Other standard product parameters and features offered in discrete steps include but are not limited to base curve radii, diameter, stabilization profiles and thickness profiles.

"Substrate" as used herein, refers to a physical entity upon which other entities may be placed or formed.

"Substructure" as used herein, refers to topological features or parameters that are capable of supporting and sometimes influencing at least a portion of fluent lens reactive media in a lens precursor. The substructure may include one or both the substrate and one or more lens precursor features included for the particular lens design.

The control of the fluent lens reactive media may include, for example, regulating the amount of lens reactive media in the lens precursor in one or more sections and influencing the resulting optical properties of the free-formed ophthalmic lens.

"Target File" as used herein and sometimes referred to as "Target Lens Design," refer to data that represents a lens design, a thickness map, a lens precursor design, a lens precursor feature design, or combinations of the above. A target file may be represented in either a hydrated or un-hydrated state, in flat or curved Space, in 2-dimensional or 3-dimensional space, and by methods including but not limited to, geometric drawings, power profile, shape, features, thicknesses etc. Target files may contain data associated with a regularly or irregularly spaced grid.

"Thickness Map" as used herein, refers to a 2-dimensional or 3-dimensional thickness profile representation of a desired product, or lens precursor. Thickness maps may either be in one or both of flat space coordinate space and curved space coordinate space, and may contain data associated with a regularly or irregularly spaced grid.

"Volumator" as used herein, refers to a feature that controls the flow of the fluid reactive mixture in relation to an outer edge of the lens precursor, or another feature or region of the lens precursor. A volumator may allow one or more of the following: desired heights, depths, angular widths, lengths, shapes, and angles, etc., of minimal energy surfaces to produce desired lens precursor geometries. Parameters defining a volumator are in many cases selected based at least in part upon parameters defining adjacent lens features and a desired lens shape.

"Voxel" as used herein, also referred to as "Actinic Radiation Voxel" is a volume element, representing a value on a regular or irregular grid in 3-dimensional space. A voxel may be viewed as a three dimensional pixel, however, wherein a pixel represents 2D image data a voxel includes a third dimension. In addition, wherein voxels are frequently used in the visualization and analysis of medical and scientific data, in the present invention, a voxel is used to define the boundaries of an amount of actinic radiation reaching a particular volume of reactive mixture, thereby controlling the rate of crosslinking or polymerization of that specific volume of reactive mixture. By way of example, voxels are considered in the present invention as existing in a single layer conformal to a 2-D mold surface wherein the actinic radiation may be directed normal to the 2-D surface and in a common axial dimension of each voxel. As an example, specific volume of reactive mixture may be crosslinked or polymerized according to 768×768 voxels.

The present invention includes methods and apparatus for forming a lens precursor comprising topological features as part of a substructure of a lens precursor form/lens precursor. The substructure may function to control of at least a portion of the non-polymerized or partially polymerized fluent reactive media portion of the lens precursor. Said lens precursor which may be further processed into an ophthalmic lens.

Lens Precursor Features

Many types of ophthalmic contact lenses can be much more complex ophthalmic lenses than it would be expected from their appearance and as currently utilized. In some types of ophthalmic lenses, underlying features may be essential to allow for peak performance, comfort, and different functionality. In the description of the inventive art herein, a number of such features that are relevant to the art of fabricating ophthalmic lenses in a free-form manner are described. After a description of some of the novel aspects and the nature of these features, a description will then be made that portrays how, in exemplary embodiments of the invention, the features may be formed, act, and interact with each other and the use of an exemplary free-form process that can allow for desired aspects of a desired product or a target lens design. This then provides a basis for describing some exemplary methodology consistent with the inventive art herein.

Proceeding to FIGS. 1A and 1B, it may be apparent that cross sectional depictions demonstrate the level of complexity that the collection of features may define. The two figures depict a fundamental aspect of the free-form art; namely, the lens precursor. A lens precursor, as its glossary definition provides the full definition for, is a combination of a polymerized region(s) above a gel point in combination with non-polymerized or partially polymerized regions below a gel point fluent lens reactive media. The non-polymerized or partially polymerized below a gel point fluent lens reactive media may provide the framework for generating ophthalmic lens products with high optical performance.

Flowing across a gelled substructure, at least a portion of the fluent lens reactive media may flow to a particular state, for example, a minimum energy surface state. This may produce a much smoother surface that can allow for the creation of desirable optically active regions but also can add to the complexity of generating the overall lens product. For example, using novel free-form design and production technology may enable the lens product using aspects of fluent lens reactive media in conjuncture with the substructure.

Referring back to FIG. 1A and FIG. 1B, FIG. 1A depicts a gelled substructure cross section of an exemplary lens precursor alone in flat space, sometimes referred to as the lens precursor form. FIG. 1B depicts the same substructure, also in flat space, along with a fluent lens reactive media layer upon the gelled substructure.

In FIG. 1A, a side view cross-sectional representation of an exemplary lens precursor form 100A is depicted in flat space where the natural three-dimensional curvature of ophthalmic lens devices is removed so that the thickness of the features themselves may be clearly envisioned. The exemplary cross section includes a collection of different lens precursor features. The lens precursor form 100A may comprise one continuous lens edge 110A. This feature may be described as continuous to define the fact that the lens edge abuts and may connect to its neighboring features as shown as item 115A in the cross sectional FIG. 1A. It may also help in understanding the nature of this lens precursor edge feature, as in some implementations, it may exist all around the periphery as depicted in FIG. 1E item 110E.

Continuing with features demonstrated in FIG. 1A, at 115A a continuous stabilization zone feature is depicted. This stabilization zone feature when viewed in a plan view, FIG. 1E is represented as items 115E on either side of the exemplary lens. As previously mentioned, these types of lens precursor features may be important in providing different functions. In particular, the stabilization zone features may be important, for example, in providing the function of locating the ophthalmic lens in a correct location and/or orientation when it is on the eye of a user. In some stabilization zone features, the feature may assume a shape that has a larger thickness to perform its function, as shown in the left side of FIG. 1A, item 115 A. Additionally, it may be apparent from observing the exemplary representation which includes fluent lens reactive media 135B in FIG. 1B, that fluent lens reactive media in the region of feature 115 B may have particular effect due to the topological aspects of the regionally thicker nature of the stabilization zone feature, 115B.

Continuing across the exemplary cross section, FIG. 1A, at 120A an exemplary continuous volumator feature is depicted. As described in further detail in subsequent sections, the shape of this feature may include various implications. In the location of this cross section, this feature 120A on the left side of the cross section may be made up of two parts, a lower shelf, and a second higher shelf that abuts the high thickness region of the stabilization zone feature 115A on the left side of the cross section. Alternately, on the right side of the cross section where the stabilization zone feature 115B may not be so thick, the volumator feature 120B may be a simple shelf at about the same thickness as the Stabilization Zone. By the nature of some fluent lens reactive materials, this exemplary difference in the cross section of the volumator next to features of different heights can enable desired resulting properties of the end product. For example, the volumator can require having more "volume" potential for fluent media to flow into next to relatively thick topological features.

At 125A, an optic zone is depicted. The optic zone or a portion thereof may reside on an ophthalmic lens user's eye in front of the portions of the eye where light may pass into the eye body. Moreover, the combination of the optic zone substructure 125B and fluent media 135B in the optic zone may create combined thickness profiles that may result in the desired optical properties of the entire optic zone.

Yet another feature characteristic can be a lens edge. A lens edge may be present on an outer edge of a lens precursor and may be the same or different heights or angular widths all of the way around a lens precursor. The lens edge may be continuous around a lens precursor, or may be present in discrete, non-continuous zones. The lens edge may act like a fence structure to provide a well-defined edge that may contain fluent lens reactive media and can keep it from flowing or control the flow over an edge of a lens precursor during various stages during the fabrication of a lens.

In FIG. 1A, the height of a lens edge 110A on a lens precursor may range from 0.001 mm to 1.000 mm to provide at least portions of the desired substructure, said substructure that may be capable of influencing the fluent reactive media near the edge of a lens precursor. The definition of the regional shape or height profile may be achieved by a variety of methods including the increasing of intensity, wavelength, or time of actinic radiation exposure of monomer mixture in a particular location to result in higher regions and conversely the opposite relative adjustment to result in lower regions. These higher regions may function, for example, to have a higher lens edge in some discrete parts of the defining edge to control the fluid lens reactive media and accordingly, provide a lens that comprises a thicker lens edge in those portions.

The lengths of the lens edge may also differ in different designs and may include lengths that may range from 0.001 mm to 2.00 mm. The lens edge may be continuous around the perimeter or be present in segmented sections as per the target design. Accordingly, the length of the edge feature can form a minimal energy surface for the fluent lens reactive mixture.

At 115A, a continuous stabilization zone topological feature is depicted. stabilization zone topological features may be present in a lens precursor accordingly and include height or thickness ranges of about 0.050 mm to 1.000 mm, and ranges of lengths of about 0.001 mm to 4.500 mm. These stabilization zones may also assume a great diversity of design aspects and may be continuous, segmented, or non-continuous. For example, one stabilization ring can be present which includes two proportionally large protruding regions for stabilization functionality.

At 120A, a volumator topological feature is depicted. As mentioned, the volumator feature may aid in the controlled flow of fluid reactive mixture between one or more regions of the lens precursor. Consequently, when the feature may be defined with a locally emptier volume of gelled material, the flow of fluent media may be characterized as being "controlled." Where there is controlled flow, a greater volume of fluid lens reactive mixture may be present therein; which may thereby allow for a larger volume of fluid lens reactive mixture to be subsequently cured in those areas of the lens precursor.

The volumator may be continuous around a perimeter or non-continuous. The height or thickness of the volumator may include portions with ranges from 0.001 mm to 1.000 mm and ranges of lengths from 0.001 mm to 4.500 mm.

Referring again to FIG. 1B, a cross-sectional representation of a lens precursor 100B that includes single lens precursor features of multiple types and heights 105B are illustrated. The lens precursor may include a single, continuous lens edge 110B, a single, stabilization zone feature 115B, a single, continuous volumator feature 120B, a single, continuous optic zone 125B, a minimum energy surface 130B, and fluent lens reactive media 135B. As depicted, the minimum energy surface 130B may be created by reactive media polymerized at or above a gel point to form a lens precursor with features that may act individually, or with each other, to create a minimum energy surface for fluid lens reactive media to sit on and be at a lower and sometimes at a minimal surface energy state 130B. As depicted, minimal energy surfaces can be smooth and continuous surfaces. However, it is possible to implement the invention so that the minimal energy surfaces may be in smooth discrete segments.

Accordingly, the present invention leverages the concept of a minimal energy surface which may derive its shape as a result of the ways in which fluent lens reactive media may sit and flow over a substructure of a lens precursor form. Consequently, the flow and amount of fluent lens reactive media that sits on or adhere to a particular portion of a lens precursor form may be influenced by the shape and topology of that lens precursor form. For example, lens precursor features in the lens precursor form may not in their own right create a smooth and continuous profile; however, a resulting lens precursor may indeed be smooth and continuous when viewed as the combination, item 105B, of the lens precursor form and the fluent lens reactive media. This concept will be explained further in subsequent sections herein.

Referring now to FIG. 1C, a cross-sectional representation of another exemplary lens precursor 100C that includes different types of lens precursor features 105C is illustrated. A characteristic difference in this lens precursor design; however, is that some of the features depicted may occur one time in the design whereas other features may occur numerous times.

In the exemplary lens precursor 100C, the lens precursor includes a single lens edge 110C, multiple stabilization zone features 115C, multiple volumator features 120C, a single optic zone 125C, a minimum energy surface 130C, and fluent lens reactive media 135C. In some cases like the multiple versions of the stabilization zone features, a single cross sectional depiction may demonstrate at least two different versions of the lens precursor feature, as for example, the volumator that appears to the left of the leftmost stabilization zone feature depicted and the volumator that appears to the right of that stabilization zone feature.

Multiple versions of features may be more apparent by observing a plan representation of the device. In a more general sense, a great diversity of embodiments of lens precursor designs may exist that may derive from multiple occurrences of certain lens precursor features. (The multiplicity of the specified features is not limited to stabilization zones and volumators as the design may include more than one of any of the above-mentioned features depending on the target lens design of a particular product).

Figure 1E:
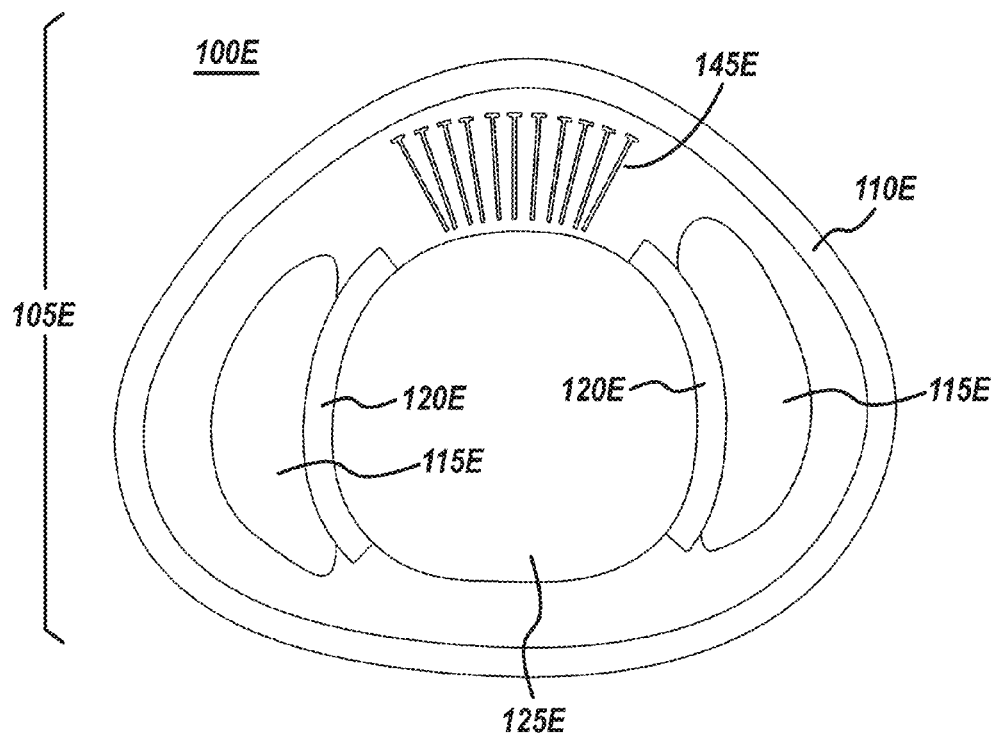
FIG. 1E illustrates a top view of an exemplary non-round lens precursor that comprises single and multiple types of lens precursor features, in addition to drain channel features.

Referring now to FIG. 1D, a cross-sectional representation of a lens precursor 100D that includes different types of lens precursor features 105D occurring in single and multiple instances per design and in addition to a moat feature 140D is illustrated. In the present exemplary lens precursor 100D, a single lens edge 110D, multiple stabilization zone features 115D, multiple volumator features 120D, a single moat feature 140D, multiple Optic Zones 125D, a minimum energy surface 130D, and fluent lens reactive media 135D are included. It is apparent to one skilled in the art, that very complex ophthalmic lenses may be designed when individual lens precursor features are combined and organized together to enable target lens designs.

As depicted in FIG. 1D, a moat feature 140D represents another type of lens precursor feature or topological feature that can be included in designs. Similar in some manners to volumators, moat features may be significantly lower in height than surrounding features and may typically be formed. A moat may be extended into or be a part of another feature, such as, a volumator. Additionally, a moat may consist of a section that is below a gel point in the lens precursor (and hence be defined in the portion of the lens precursor that has reached the gel point).

Referring now to FIG. 1E, a top view representation of the structure of an exemplary non-round lens precursor 105E that includes single and multiple different types of lens precursor features is depicted. Also visible in a top view but not discussed as yet in the prior cross section related discussion, another type of lens precursor feature called a drain channel 145E. The drain channel features 145E may help reduce a volume of one or more reduced gelled feature(s). Thus, the nature of the shape of the drain channel may be such as to draw additional volumes of fluent lens reactive mixture away from a particular region.

In the present, exemplary lens precursor 100E, a listing of all the lens precursor features that may be seen from a top view perspective includes drain channel features 145E, a single lens edge 110E, multiple stabilization zone features 115E, multiple volumator features 120E, and a single optic zone 125E.

The drain channel feature(s) 145E may be generated by reducing the actinic radiation exposure in one or more voxel location(s) by decreasing the exposure signal given in a DMD instruction(s) at these locations. In an analogous manner, the drain channel feature(s) may also be formed by increasing the actinic radiation exposure in one or more voxel location(s) by increasing the exposure signal given in a DMD instruction(s) at these locations. In either case, the relative change in actinic radiation exposure would create relative depressions that may occur in the straight line type shapes similar to those of items 145E. Furthermore, from a more general perspective, the drain channel feature(s) may be of a shape that may enable fluent lens reactive media to do one or more of the following: flow across, away from, and settle on, all or at least a portion of a polymerized lens precursor, lens precursor form, or another other lens precursor feature(s). The drain channel topographical feature may include, for example continuous or discrete segmented depressions in portions of the gelled portion of the lens precursor.

Varied Characteristics of Lens Precursor Features

An additional aspect of the present invention comes from the changes in form and function of ophthalmic lenses that may derive from variations of one or more parameters of one or more lens precursor features, for example, including varying one or more of height, depth, angular widths, length, shape, and location. Furthermore, the same variations in ophthalmic lens characteristics due to variations in the parameters of lens precursor features also create additional inventive art when they are combined in various manners described herein.

Lens precursor features may be parametrically controlled based on empirically defined relationships between these features and desired lens characteristics, and these features may be mathematically or empirically related to other lens precursor features. For example, the design of a volumator feature may be empirically linked to stabilization zone features to create smooth and continuous surfaces relationships between them and therefore assist in the determination of appropriate design choices that incorporate these features in combinations and thereby end up with the designed lens properties or function.

More importantly, other uses of the lens precursor features may include, for example, influencing the flow of at some portions of the fluent lens reactive media. Lens precursor features may additionally be utilized for alignment and calibration purposes of lens precursor fabrication.

Additional features may include marks which may be defined into the gelled material and may become visible under inspection. These marks may be then used in the fabrication process. For example, substrates used in a free-form process may need to be precisely centered in order to manufacture a desired lens precursor, ophthalmic lens, or lens precursor features. The marks defined into gelled material by the imaging system may be viewed and compared to a targeted location(s) of the marks to then provide alignment of the imaging system to the physical Substrate.

Lens precursor features may also be used to determine optical magnification of free-form equipment. In a non-limiting exemplary sense, by defining marks into the gelled material, for example by using the imaging system and a particular target size, then the marks may be subsequently measured to then provide the resulting measured mark versus the imaged size to allow for the determination and control of the magnification of the system. This may be important with free-form manufacturing processes, as optical magnification values may be required to ensure that one or more of height, depth, width, length, shape, and location of features may be fabricated as desired.

Optical magnification together with the marks may be useful in determining and controlling an accurate positioning of the substrate. For example, where lens precursor features may be used for one or more of alignment, calibration, and optical magnification determination, Marks may be measured via imaging techniques, including wavefront technology.

Figure 2:
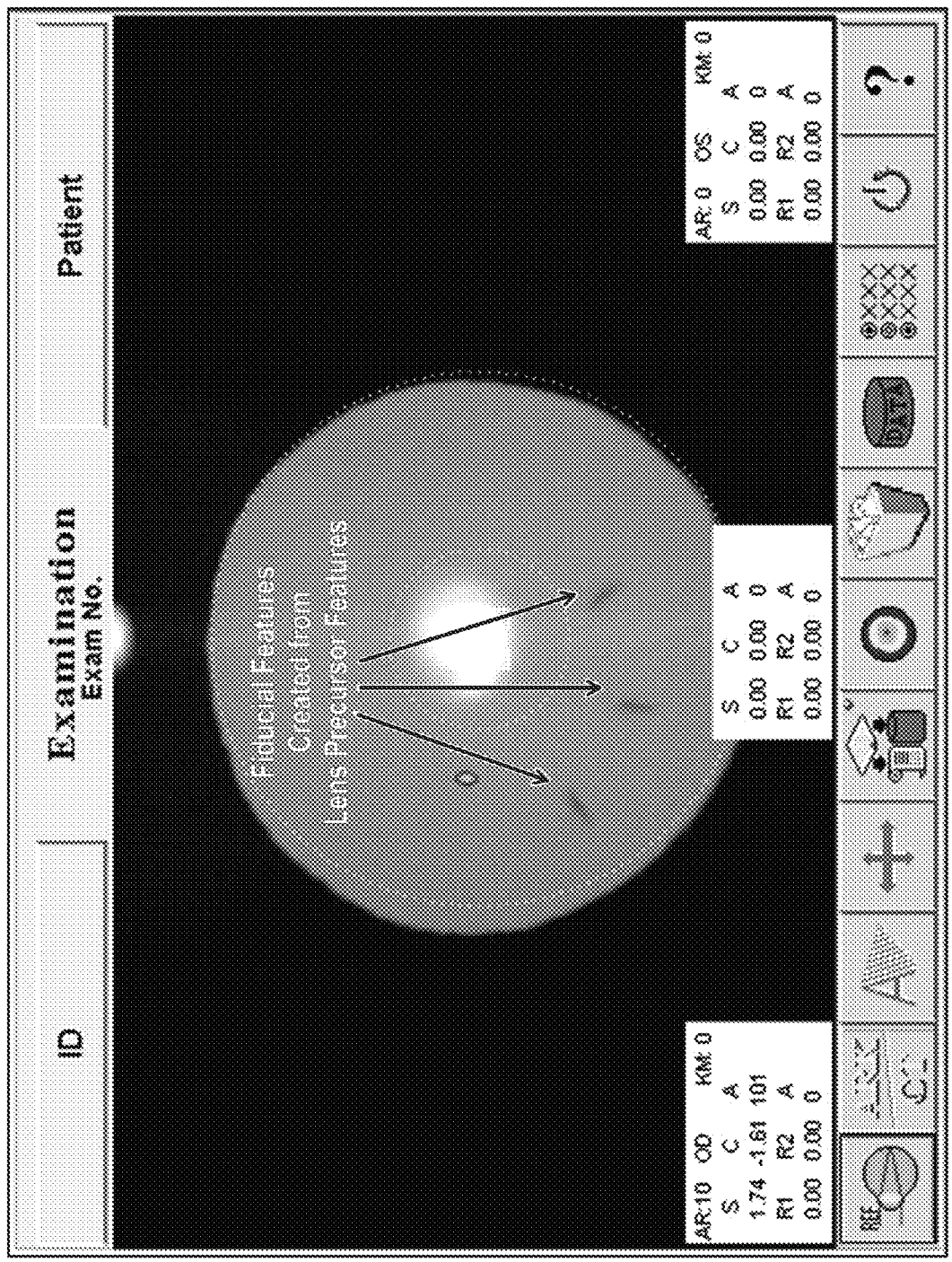
FIG. 2 illustrates an example of a representation of an image depicting formed marks on a lens.

The marks can include fiducial marks, also referred to as orientation marks, which can be defined by lens precursor features and parameters, and fabricated on lens precursors using free-form methods. Fiducial marks may be used to determine one or more of; on-eye lens location, centration, rotation, and movement. Furthermore, imaging techniques and wavefront technology can additionally make use to help determine one or more of location, size, and shape of fiducial marks. An image depicting fiducial mark detection on a lens on eye is illustrated in FIG. 2.

The mark features may even be formed into characters, such as, in a non-limiting sense letters or numbers to convey information. Other types of mark features conveying information may derive from bar codes or other optically recognizable character features. There may be numerous uses for character type features to be formed into an ophthalmic lens precursor such as for example, the creation of anti-counterfeiting features and product lens identifications.

Additional functionality of lens precursor features may include creating optic zones that result in topology that is both of optical grade and at the same time provides corrective aspects to vision of a user, as this is a major purpose of free-form processes. By controlling the topology of gelled surfaces, for example on a pixel-by-pixel basis, and by controlling the characteristics of the fluent media over these gelled surfaces and neighboring lens precursor features, a particular desired corrective surface can be formed. However, it will be apparent to one skilled in the art that flat surfaces of gelled material with various shapes including for example round features may, in some cases and with certain fluent media characteristics, form small nearly spherical shapes of fluent media that when fixed with actinic radiation form a feature called a lenslet. If these features, in isolated form or in an array form occur on the lens precursor they may have the effect of modifying the optical power of the regions they cover.

Interactions Between Two or More Lens Precursor Features

As mentioned in previous sections, the dynamics of flow of fluent lens reactive media may be a complex function of the fluent media itself, and numerous other factors, including the shape and topology of features surrounding a particular region. In another related aspect of the present invention, the effect of neighboring features may be exploited by adjusting the control parameters of these neighboring lens precursor features. As well, since these adjusted parameters may affect the fluid dynamics of the fluent lens reactive media, the surface that results after the fixation of the fluent media may also be affected by these changes in the design parameters of lens precursor features. As a specific non-limiting example, the angle that fluent lens reactive media may create as it bridges from an optic zone to a stabilization zone feature may be controlled by modifying the control parameters of a volumator feature and/or the control parameters of an optic zone.

If the height of the volumator is decreased in its location between the neighboring stabilization zone feature and the neighboring optic zone, the change in form which the fluent lens reactive media takes spanning between these two features and above the adjusted volumator may be considered and accounted for in the design. This is but one exemplary type change where a lens precursor feature change may affect the fluent media above and around other neighboring features and there may be other types of changes which can cause a particular desired effect.

Another non-limiting example may be described with reference to an astigmatic optic zone where the thickness in the 0 degree plane is different to the thickness in the 90 degree plane. The optic edge may, for example, be 100 microns thick in the 0 degree plane, and 150 microns thick in the 90 degree plane. In the lens precursor form, as has already been described, such an optic zone may be surrounded by a volumator feature outside of which there may be one or more stabilization zones, for example 400 microns in height. If the stabilization zone and the highest point (150 microns) on the optic zone are angularly aligned, fluent lens reactive media will form a bridge from the 400 microns high stabilization zones to the highest point on the optic zone over the volumator feature. If the same geometry and features are used, but the optic zone is now rotated by 90 degrees and the volumator and stabilization zones stay in the same orientation as before, the fluent lens reactive media will now bridge differently from the stabilization zones at a height of 400 microns to the optic zone edge that is now 100 microns high. Thus, the angle that fluent lens reactive media may create as it bridges from an astigmatic optic zone to a stabilization zone feature may be controlled by modifying the control parameters (angular alignment) of the stabilization zone or the optic zone.

Yet another example would involve changing the location of the drain channel features relative to other features, so that the effect of the volume being drained is different. For example, if the drain channels of FIG. 12 were extended into the very center of the optic zone, fluent lens reactive media would be drained from the very apex of the lens as opposed to the effect of the drain channels shown, that are not extending into the optic zone and thus will not drain from the optic zone to the same extent. If for example there is a lake feature in the optic zone, and no drain channels extend into the optic zone, then the lake feature cannot be drained. Thus, changing the depth, width, size and extent and location of drain channels affects the shape to which the fluent lens reactive media will settle in a given period of time.

In different free-form processes, processing of a lens precursor can include stabilization and fixing of the fluid lens reactive mixture portion on the lens precursor to form a lens. A controlled amount of fluent lens reactive media may be left on a surface of a lens precursor form during separation of a substrate and a lens precursor form from a reservoir containing excess reactive mixture. In addition to the lens precursor features, which may help control the amount of fluent lens reactive media that sticks to the gelled portion, the combination of the reactive mixture, speed of removal, and/or control of environmental factors (e.g., temperature, oxygen level, etc.) can be changed to control the amount of fluent reactive mixture that is present in the formed lens precursor. Also, a portion of the reactive mixture may be wicked, or to the contrary, additional fluent reactive mixture may be added to the lens precursor using one of many methods known by a person skilled in the art. Each of these possibilities may create different base conditions that effect the interaction of different lens precursor features, their design aspects respectively and the nature of the fluid dynamics of the fluent reactive media upon the underlying substructure of lens precursor features.

In some free-form methodology, once the amount of fluent reactive mixture is on or proximate to the lens precursor and, where appropriate, after a stabilization step, a fixing process may be initiated to obtain the desired lens in an unhydrated state. In accordance with the foregoing lens precursor features explanations, some of the surfaces may not become a contiguous lens until fluent lens reactive media is fixed accordingly. For example, where there is a moat in a portion of the lens precursor form with a zero thickness. In the case of a zero thickness moat, the gelled features may end at the near periphery of the moat feature. Under some conditions, fluent media can remain in the moat portion when the lens precursor is removed from contact with the reservoir of reactive media. Additional fluent media from regions surrounding the moat region may then also flow into the moat region. Nevertheless, until this fluent media is fixed there may not be gelled material in this region, but after fixation the moat region may be subsequently included as a portion of the gelled lens product after subsequent processing.

Methods of Forming a Lens Precursor with Lens Precursor Features

Referring now to FIG. 3 (item 300), exemplary method steps that may be used to implement certain exemplary embodiments of the present invention are illustrated. In the previous discussion, there have been descriptions of numerous types of lens precursor features that may be included in a lens design. The exemplary method steps provide means of designing lenses which may incorporate all or some of these various features.

At 301, patient data may be collected. Collection of data may occur at different times and using one or more of the many known techniques in the art. For example, physical data can be collected through a topographical exam which may yield guidance on product base curve, diameter and thickness options, an over-refraction exam which may yield low order optical aberration(s) such as sphere power, cylinder power, and cylinder axis, and/or a wavefront exam which may yield medium and higher order optical aberration requirements including one or more of spherical aberration, trefoil, coma, and pentafoil. Additional data may include data, such as, patient's information obtained through questionnaires and/or data obtained from an image received.

At 302, one or more subsets of patient data may be selected to identify optical aberrations. Identified optical aberrations may be used for the selection of a suitable standard product design or a custom product design. Generally, standard products are offered in discrete steps and may require some user accommodation to the difference between the more exact needs and the closest available standard product. When a custom product design is made a custom product may include one or more parameters that may be available in selectable values that may be between standard product incremental steps or otherwise different from standard product definitions.

Accordingly, Custom product parameters may allow for more precise sphere power, cylinder power, and cylinder axis (e.g., −3.125D/−0.47D×18°) than standard products and may include base curves, diameters, stabilization profiles, and thickness profiles based upon a particular product offered and its intended use. For example, the results of a collection of a particular patient's data in step 301, analysis of the data in step 302 may result in determining that a desired product may provide for astigmatic correction and in some cases for a prescription where the correction is desired for a custom product with specification of parameter requirements for more precise sphere power, cylinder power, and axis.

At 303, mechanical parameters including one or more of desired base curve, diameter, and center thickness can be selected. If it is determined that a free-formed lens may be appropriate, at 304 one or more lens precursor features and defining parameters may be selected based upon one or both of optical selections 302 and mechanical parameter inputs 303.

Continuing with the example discussed with reference to step 302, it may be determined that the lens design may require lens precursor features including stabilization zones to keep the astigmatic correction oriented appropriately. Furthermore, it may be desired that the lens have a single lens edge around the entire periphery of the lens. Due to the nature of the optic zone astigmatic correction, in an exemplary sense, it may be determined that multiple volumator features may be required to reach a desirable optic zone design and/or fabrication.

To identify the lenses, it may be determined that markings of various kinds would be placed onto the feature design. Finally, again in an exemplary sense, it may be determined that drain channel features would also improve the design and/or manufacturing aspects of the optic zones.

At 305, target lens thickness maps and their associated files (which may contain a numerical representation of the thickness map in a datafile format) may be generated or identified from a database. At 305 the resulting definitions of the optic zone needs of step 302, the mechanical definitions of 303, and the complement of the lens precursor features of step 304 may be consolidated into a model. The model would determine the theoretical thickness by design that would appropriately perform the desired function of the various regions. From the model, thickness maps and associated files may be generated. As may be clear from earlier sections, the generated designs and files may result from one, or a plurality of desired lens precursor features and the desired fluent lens reactive media surfaces for a target design.

Figure 4:
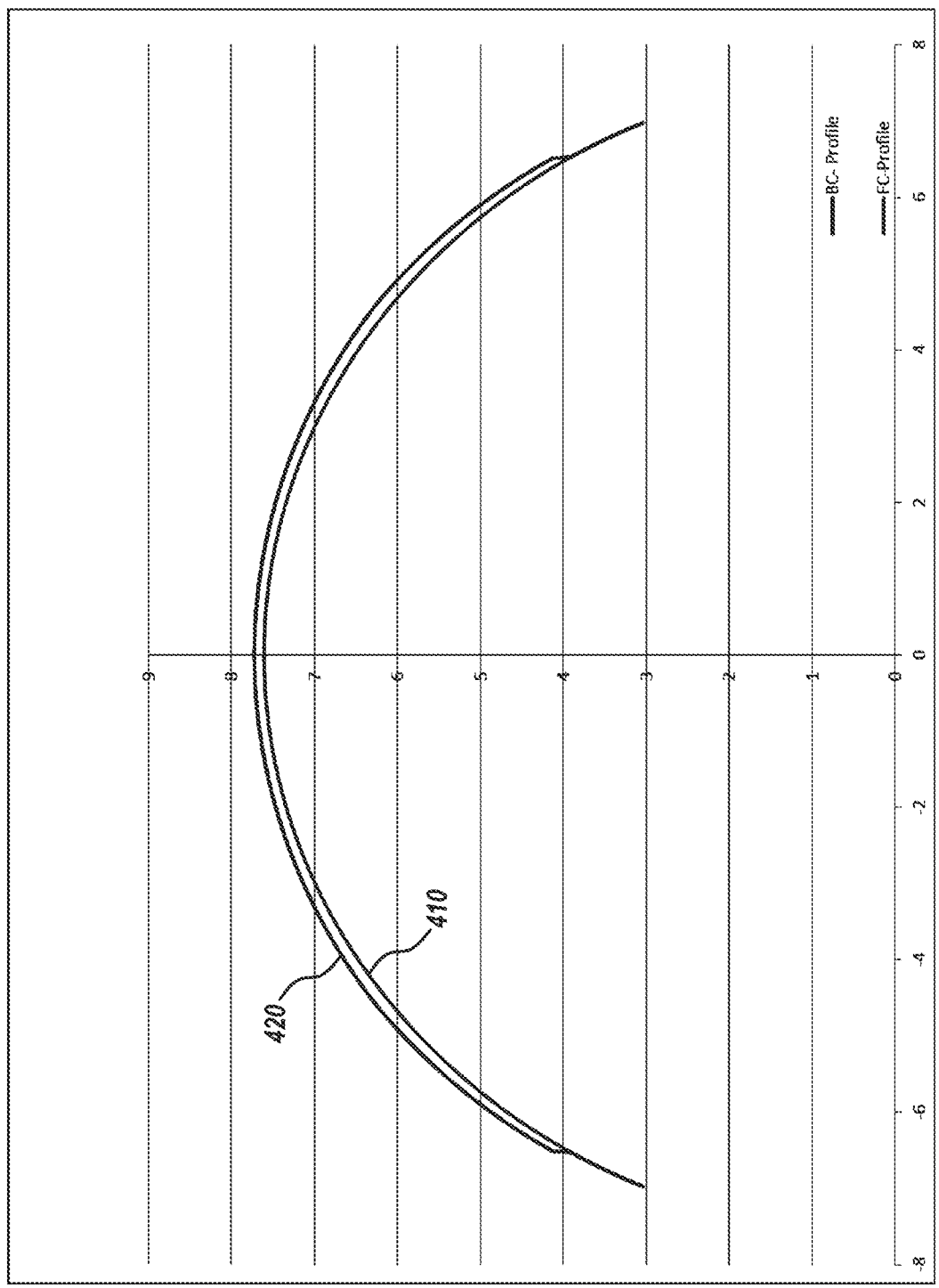
FIG. 4 illustrates an exemplary screen shot generated by software program(s) depicting of a cross-sectional representation of a target file in curved space.

To provide some illustration of the type of results that may come from step 305, a cross-sectional representation of a target lens thickness map may be found in FIG. 4. The depiction shows the lens design in curved space. At 410, a representation of the back curve profile may be found. At 420, the Front Curve profile may be found. When an associated file to this thickness map is referenced, it may be a datafile that contains location variables in various coordinate systems such as Cartesian coordinates, Polar Coordinates, Spherical Coordinates or other known mathematical coordinate formalisms. In the associated file for each of the coordinate representations may also include thickness values of some kind.

Referring now to FIG. 5, an example of an associated datafile where the coordinates are indicated in Cartesian coordinates is given. Target files and/or lens designs may be created by combining select optical and mechanical requirements, together with other features (e.g., a type of stabilization mechanism such as a stabilization zone).

Figure 6:
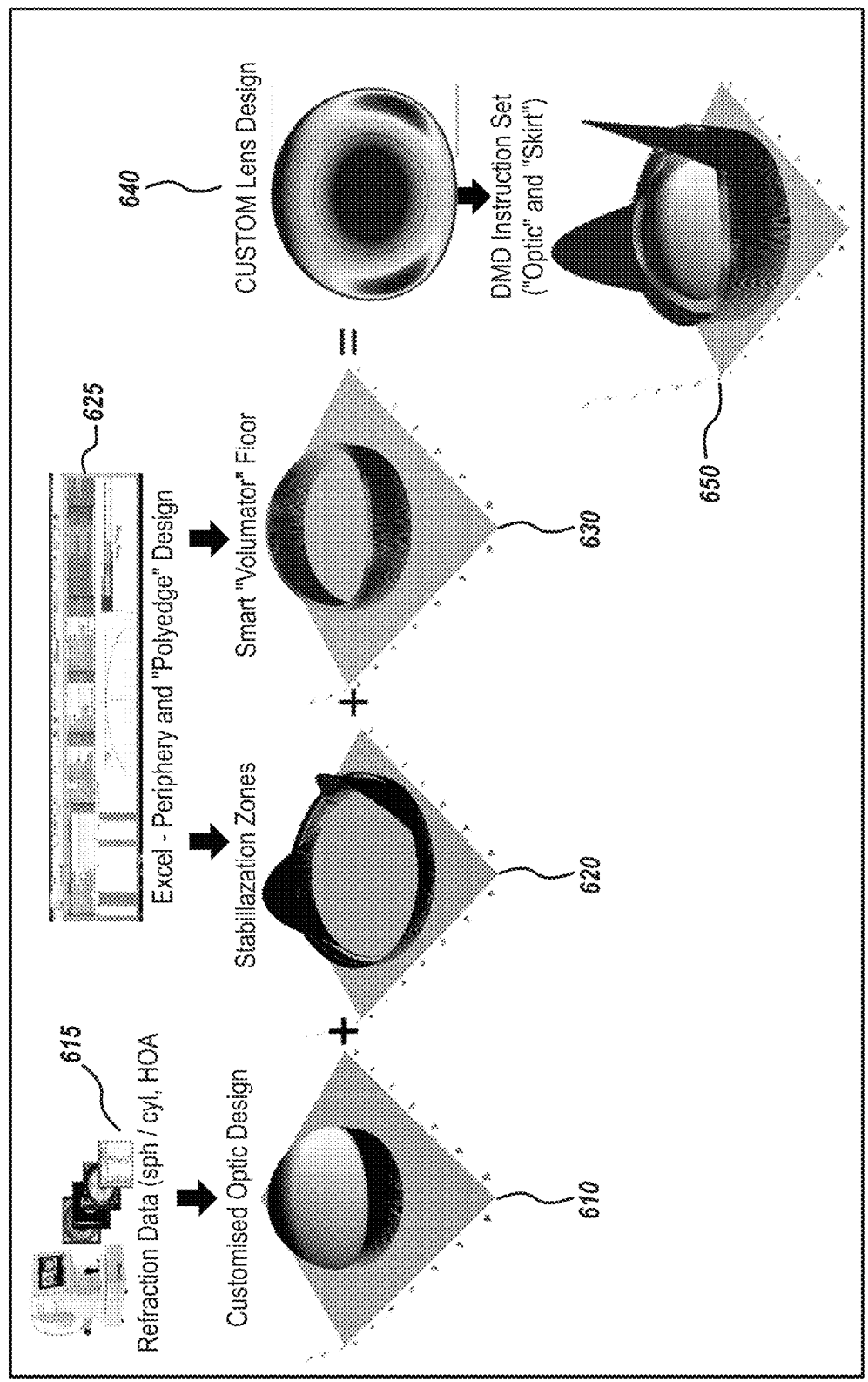
FIG. 6 illustrates an exemplary screen shot generated by software program(s) used to create and output desired optical and mechanical features, which may be utilized to generate target file.
Figure 6A:
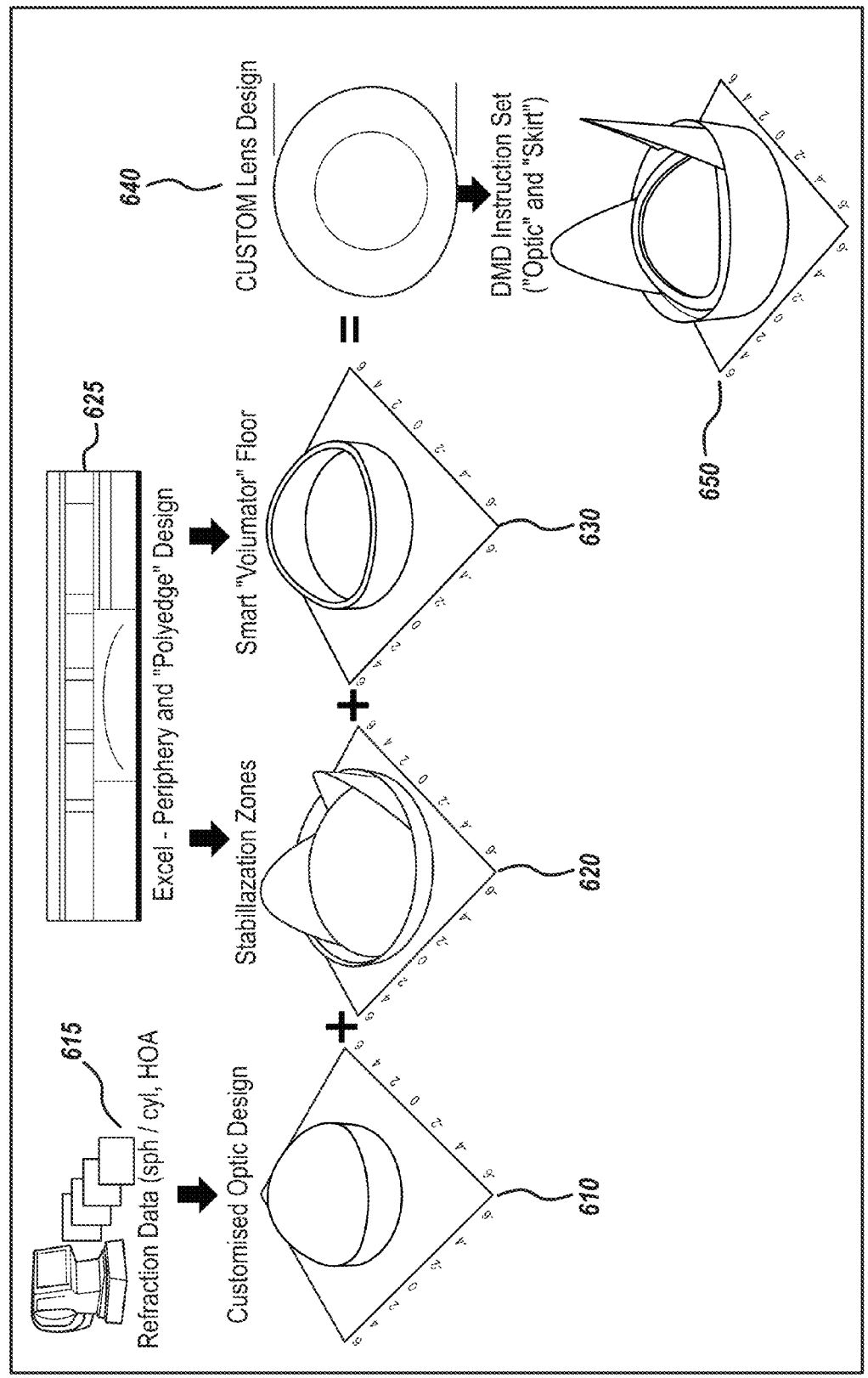
FIG. 6a is a schematic drawing of the exemplary screen shot of FIG. 6.

Referring now to FIGS. 6 and 6A, an example of utilizing multiple software programs to create and output desired optical and mechanical features to generate a target lens design is illustrated. At 610, a model of a customized optic design is presented where the representation may relate to the target thickness of the design. The design can result from output from the collection of refractions data as shown in item 615.

At 620, Stabilization Zones, and in item 630, a Smart volumator Floor design may be constructed as output from an excel based spreadsheet design as shown by item 625, for example the spreadsheet including sets of data points as Cartesian coordinates. These three model elements may be combined to result in a custom lens design depicted in item 640. There can be a large number of methods to formulate lens designs from various elements and methods of modeling those elements and should not be limited by the particular example given.

As an alternative, the calculation that is performed at step 305 may result in a waveform target rather than a thickness target. Such a target design may be useful in some cases since the metrology may directly result in a waveform output. Similar utility of the target lens thickness maps that may be generated in step 305 may occur for target lens waveforms.

At 306, a model is formulated to generate lens precursor forms that may appropriately result in a lens precursor that matches the thickness targets or the waveform targets formed in step 305. There may be numerous means to generate lens precursor form design thickness maps. In some instances a kinetic fluent media model may be applied which may model the manners that fluent media may flow over solid gelled substrate material.

Alternately, an entirely empirical algorithm may result in estimations for the lens precursor form thickness pattern that may be required to result in a target lens design after the fluent media reaches a stable state based on prior results of lens making processing. It is apparent to one skilled in the art that numerous modeling techniques that may include combinations of dynamic modeling algorithms, and also, empirical models may be used to convert a target lens thickness map into the model. As a result, target lens designs, thickness maps and associated files for a desired product may be generated from lens precursor designs, thickness maps and files.

In a general sense, a target file, or portions thereof, may be created at least in part by utilizing one or more of traditional 2-dimensional design methods, 3-dimensional design methods, empirical methods, and by combinations of both traditional and empirical methods. Examples of traditional methods may include one or more of ray tracing, mathematical formulae, CAD/CAM/CAE, 2D modeling software, 3D modeling software, computer programming languages, Microsoft Excel, static modeling, fluid modeling, and computational fluid dynamics software.

At 308, DMD shows including a DMD sub-sequences, which may refer to the first generated DMD show from a series of shows created by iteration, may be generated. Referring back to FIG. 6, an exemplary representation of the modeled cumulative intensity dosing desired to be performed is represented as item 650; which may have been calculated based on the custom lens design, 640 discussed in earlier sections.

Based on models that correlate intensity and time of actinic light exposure to a reactive monomer mixture to be utilized, values of intensity and time may be calculated on a voxel by voxel basis. These values may be used to create a DMD show that may execute control of a light system with a DMD to expose an appropriate Substrate to the calculated actinic radiation exposure on a voxel by voxel basis. Additionally, there may be numerous methods for converting the needed time and intensity values into a DMD show or DMD subsequences.

In a non-limiting sense, the DMD show(s) may use grey scale modulation to deliver variable exposures to voxels that relate to the calculated exposure. Alternate methods may include exposing voxels for maximal intensity exposures for a particular duty cycle or percentage of time of the entire DMD show. If each voxel has a calculated percentage of time, then the DMD show may be similar to a movie where a number of frames is determined for the entire DMD show (which may be called a "movie") and then the percentage would relate to the ratio of the number of frames at a particular voxel location that have high intensity to the total number of frames.

When the DMD show is used to control the actinic radiation exposure system, which may include a DMD as the light modulation element, a lens precursor may be formed upon a substrate in step number 309. After this processing has occurred, the lens precursor may exist as a gelled formed material, the lens precursor form and also have upon that gelled media a layer of fluent media which has achieved a minimum energy state. Afterwards, this lens precursor may then be subjected to actinic radiation to fix the lens precursor into a completely gelled form resulting in some cases in an ophthalmic lens. Either such a lens precursor or lens may be the result of the process step indicated as number 309.

At step 310, a fabricated lens precursor or a finished ophthalmic lens may be measured for its thickness by various methods. These thickness results may then be compared to the thickness maps and their associated files which were formulated in Step 305 to determine conformance to a desired product design. As previously mentioned, the "Thickness Map" may be a wavefront-targeted map. In these cases, the measurement of 310 may obtain the wavefront data itself. Implementing other manners of measuring the thickness or wavefront information of the lens or lens precursor are within the scope of the present invention.

In some cases, the result of the measurement at step 310 may result in a lens precursor or lens that is close enough to its target lens design to be acceptable. Under such circumstances, the method shown in FIG. 3 may be complete. The result of the measurement at step 310 may, on the other hand be unacceptable. If the result is too far off from the desired target, in some cases, it may be desirable to return to step 303 and possibly make fundamental changes to the lens precursor design. Therefore, at 311, if required, a combination of optical parameters, mechanical parameters, lens precursor features, lens precursor feature parameters, fluent lens reactive media surface parameters, fabrication process conditions, thickness maps, associated files, DMD shows etc., may be added, removed, or modified and utilized in attempts to fabricate a lens precursor closer to a desired product design/design target.

Alternately, the step described above at 311 may occur when the measurement step at 310 is found to indicate an acceptable result. In these cases, the DMD show may represent an acceptable show for the generation of a lens precursor or lens with the designed characteristics. Such a show and associated design may be a desirable starting point for an altered design that is significantly close in design characteristics to the acceptable result. Again, in such cases, at 311 and 312, a combination of optical parameters, mechanical parameters, lens precursor features, lens precursor feature parameters, fluent lens reactive media surface parameters, Fabrication Process conditions, thickness maps, associated files, DMD shows, etc., may be added, removed, or modified and utilized in processing.

All of these methods may allow for additional feature changes, particularly for the Optic Zone, to be added into the method flow in a parallel manner. Proceeding to FIG. 3A (item 320), an additional step 327 may be found. In an example of the more general technique of adding in details in design into the method, a step may be included where the medium and higher order aberration corrections may be added into the target lens design at step 305 or into the lens precursor form design at step 306. It is also apparent that these separate add in elements may be used in a stand-alone fashion, where the added element 327 defines the nature of the region of the target design or the lens precursor design entirely where it has relevance.

Alternately, the added in files may be combined with the existing definitions in target lens design and lens precursor form design that have resulted in the standard method flow. The added files located at step 327 may relate to thickness maps associated with the added content or alternately as has been discussed may relate to added waveform aspects or maps for the particular region.

An alternate process that can share the similarity of the step 327 may be found by referring to FIG. 3B (item 340). In the same or a very similar manner that additional feature design aspects may be added into the method flow as thickness or wavefront targeted additions, the DMD show details may be modified by DMD sub-sequences. As shown in step 343, a non-limiting example of a DMD file may result if medium and higher order aberration corrections for a lens prescription are added into the existing DMD show directly. In some cases, a mathematical operation may be used to combine an added DMD sub-sequence. For example, an arithmetic addition operation may be performed to alter an existing DMD show or movie so for that certain defined voxel location, the sum of the voxel values at the particular locations is calculated and used to replace the value on a frame-by-frame basis. It may be possible for many other types of operations to be performed including, for example, subtractions, multiplications, divisions, Boolean operations, etc.

In a similar sense, if the DMD Sub-sequence file in step 343 defines features that add additional feature thickness or waveform equivalent thickness, then an additive process may result from including the frames of the adder DMD file to run after the existing DMD show has been performed. It may be apparent that the existing frames may be added to the DMD show at any particular location in the DMD show.

In the previous discussions relating to the methods of forming ophthalmic lenses and lens precursors with the various features that are possible and those that are mentioned, the terminology and the discussions relate particularly to the technologies relating to free-form manufacturing of ophthalmic lenses and lens precursors utilizing actinic radiation and digital mirror devices to control the details of the fabrication process. The inventive concepts herein, relate to DMD based free-form art but are also more generally applicable. For example, the step number 308 labeled DMD start show may relate to generating a control program for a stereolithography manufacturing tool.

A lens precursor may be formed using this type of manufacturing tool by using the stereolithography tool to form the lens precursor form. In a second step, for example, fluent reactive media may be added onto the lens precursor form manufactured by stereolithography. Once the fluent media is added, the combination may now define an equivalent of a lens precursor. The nature of the flow of the fluent media over the form may be similar to the flow in a voxel by voxel free-formed lens precursor. Therefore, additional methodology may derive by defining lens precursor features by different types of methods to form the basic lens precursor form which will then interact with the fluent media and are within the scope of the present invention. From a more general sense, any method including free-form voxel based lithography, stereolithography, mechanical lathing, part molding to mention a few examples, may comprise art within the scope of this disclosure.

Automation of the Design and Fabrication of Lens Precursors with Features

Figure 7:
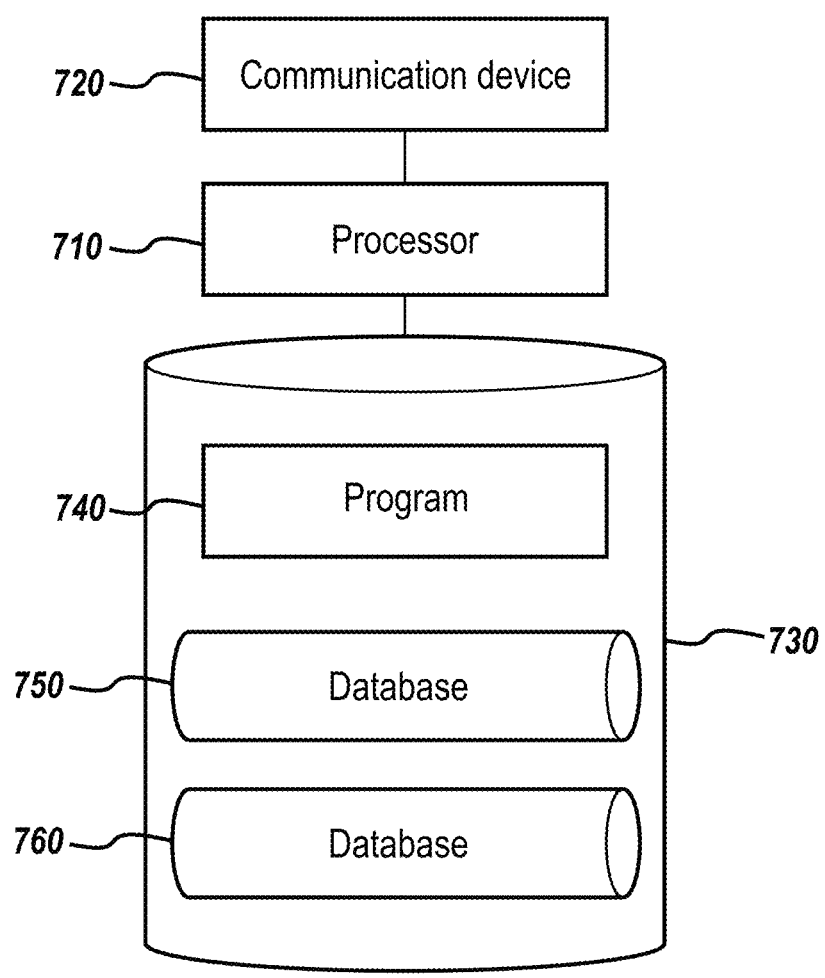
FIG. 7 illustrates a schematic diagram of an exemplary processor that may be used for some parts of the present invention.

Referring to FIG. 7, a schematic diagram of an exemplary processor that may be used for modeling software used in some parts of the present invention is depicted. The controller 700 includes a processor 710, which may include one or more processor components coupled to a communication device 720. The communication device 720 may also be configured to communicate information via a communication channel to electronically transmit and receive digital data related to the functions discussed herein.

The communication device 720 may also be used to communicate, for example, with one or more human readable display devices, such as, for example: an LCD panel, a LED display or other display device or printer.

The processor 710 may also be in communication with a storage device 730. The storage device 730 may comprise any appropriate information storage device, including combinations of magnetic storage devices (e.g., magnetic tape, radio frequency tags, and hard disk drives), optical storage devices, and/or semiconductor memory devices such as Random Access Memory (RAM) devices and Read-Only Memory (ROM) devices.

The storage device 730 may store the modeling program 740 for controlling the processor 710. The processor 710 performs instructions of the program 740, and thereby operates in accordance with the present invention. For example, the processor 710 may receive information descriptive of a target lens design, lens precursor, DMD files, patient information, lens optical performance, eye care practitioner's office data, lens precursor features, measured thickness profiles, and the like. The storage device 730 may also store and send all or some of the said information sent to the processor in one or more databases 750 and 760.

The modeling program 740 is operative with the processor 710 to cause the apparatus 700 to receive digital data descriptive of one or more optical aberrations associated with a wearer of the ophthalmic lens (FIG. 3, step 302), receive digital data descriptive of at least one desired mechanical parameter of the ophthalmic lens (FIG. 3, step 303), receive input from an operator descriptive of at least one topological feature of the lens precursor form substructure (FIG. 3, step 304) and generate a DMD show for use in a stereolithographic ophthalmic lens precursor form manufacturing tool (step 308). It may also cause the apparatus to receive digital data comprising a design thickness map of at least a portion of the lens precursor form or a lens precursor (FIG. 3, step 305 or 306), receive digital data comprising measured thicknesses of at least a portion of a lens precursor form or lens precursor manufactured by the manufacturing tool and compare the measured thicknesses with the design thickness map to determine conformance to the desired design (FIG. 3, step 310) and, if necessary, generate an alternate instruction set for use in the ophthalmic lens precursor form manufacturing tool (FIG. 3, step 311).

In the same fashion, the modeling program 740 may be operative with the processor 710 to cause the apparatus 700 to perform step 312 of FIG. 3, steps 302-308, 310-312 and 327 of FIG. 3A and steps 302-308, 310-312 and 343 of FIG. 3B.

Empirical Methods of Determining Target Files

Empirical determination of a target file or portions thereof, may involve using a free-form method to fabricate one or more of a lens, a lens precursor, a lens precursor form, and lens precursor features from which measured thickness profiles, or portions thereof, may be substituted and used in subsequent target files. For example, due to the complex nature of the fluent media and gelled form interaction, it may sometimes only be possible to fabricate desired optic zones with reduced height stabilization zone features, as compared to system designed stabilization zone features. Therefore, system calculated stabilization zone features may subsequently be replaced by corresponding measured thickness resulting profiles for the reduced height stabilization zone features that were empirically demonstrated to result in improved fabrication results.

Manners of Representing Designs in Cross Sectional Displays

Referring now to FIG. 8A, a cross-sectional representation of a non-round exemplary lens precursor 800A in 2-dimensional curved space is depicted. The exemplary lens may be classified as a single part design. By representing a top down view (item 801A) with a variety of cross sectional representations, some of the complexity of the actual topological and thickness variations may be displayed. Cross-section 805A illustrates an example of a significantly symmetrical (i.e. about symmetrical) thickness profile since with reference to a focal point of the lens, which may be in some examples the center of the optic zone, there can be a similar length of lens material from the focal point to a "right" side edge as to a "left" side edge in the cross section representation. Cross-sections 810A and 815A illustrate examples of non-symmetrical thickness profiles, since there are different lengths and thicknesses around the focal point for these directions of cross section.

A different manner of representing lenses by cross section may be understood by referring to FIG. 8B, a cross-sectional representation of a non-round exemplary lens precursor 800B in 2-dimensional flat space. (The top down representation is depicted as item 801B). In this exemplary representation, where the illustrated thickness profiles are exaggerated, the flat space representation transforms the back curve shape into a flat shape. In this type of representation, Cross-section 820B illustrates an example of a significantly symmetrical thickness profile. Cross-sections 825B and 830B illustrate examples of non-symmetrical thickness profiles.

Single and Multipart Designs—Background

Target files may be represented by one or more of continuous surface features, non-continuous surface features, and discrete features that when combined, may produce one or more of complete continuous surfaces, non-continuous surfaces, and discrete zones. For example, target files represented by one or both of single, smooth, continuous and single, non-continuous surfaces may be commonly referred to as single part designs as the shape in FIG. 3A and FIG. 3B may represent. Additionally, for example, target files may be represented by multiple discrete features. These types of design representations may be commonly referred to as multi-part designs.

Method of Using Multi Part Lens Profiles to Generate a Lens Precursor with Features As just mentioned, a target lens design can have discrete characteristics that make them candidates to be called multi-part designs. The discrete characteristics may result in a random manner as a result of a designing process, however, more typically they are formed because the design may be formed by the direct combination of different design "pieces" that relate to just a region of a full lens design. These pieces may also be considered as independent "parts" which when combined together may create a multi-part design.

Such a multi-part design concept may allow for a non-complete surface of a desired product or target file to be utilized in lens precursor fabrication. As a result, in practice a complete surface may not ever be created, stored as a single or multiple files, or transmitted to a fabrication facility.

For example, discrete, non-smooth, non-continuous data relating only to a desired product optic zone, base curve and diameter may need to be transmitted from an eye care practitioner's office to a fabrication facility in order for a desired product to be fabricated using a contour forming process technology. The transmitted data, which in its own right may represent or specify only a piece of a lens design, may be combined with other pieces for the remainder of a full design at a later time. For example, after receiving a transmission of the product optic zone design with a base curve and an overall lens design diameter, one may combine these components with a lens edge and desired stabilization zone features.

Moreover, at a different location, such as the production facilities, these additional features may be recalled from catalog items and together with fluent lens reactive media designs may complete a smooth and continuous fabricated lens precursor. Other lens fabrication techniques may require entire, complete surfaces of a desired product to be known. For example, with direct lathing of lenses, diamond tools have to follow pre-generated complete tool paths to cut an entire surface of a desired product.

Referring now to FIG. 9A, a representation is illustrated of a non-round single part design of an exemplary lens precursor 900A and cross-sectional representations in both curved and flat space. In this representation, the entire convex surface may be smooth and continuous in nature. Convex profiles of cross-sections at 905A, 910A, 915A, 920A, 925A, and 930A are also shown as smooth, continuous sections.

The designation of a design as a "Single Part Design" may be dominated by the fact that the method to generate the lens design generates the design aspects from a complete initial set of feature specifications. Therefore, the shape alone of the resulting lens may seem to have discrete parts but as they were combined together in the initial specification such a lens may still be classified as a single part design.

Referring now to FIG. 9B, representations of a non-round single part design of an exemplary lens precursor 900B and cross-sectional representations in both curved and flat space are illustrated. It may be observed that these depictions show a design in cross section, where the surface is neither smooth nor continuous in nature. Nevertheless as was indicated this may be considered a single part design and at the initial design step a feature may have been chosen which results in the non-continuous nature of the design. For example the gap in the cross section may be caused by a moat feature 990B as illustrated. Also shown are cross-sections of a surface at 935B, 940B, 945B, 950B, 955B, and 960B which may clearly show the lack of smoothness and continuity in this SinglepPart design.

Referring now to FIG. 9C, representations of a multi-part design concept of a smooth, continuous exemplary lens precursor 900C, is given. Included in the Figure are cross-sectional representations of discrete features that may make up a lens precursor design. For example, the three different features represented by 965C, 970C and 975C. A smooth and continuous convex cross-section 980C produced from this combination of discrete features may also be observed. Also shown is a plan view representation, item 901C, that depicts a smooth and continuous round multi-part design lens precursor 900C, all in 2-dimensional curved space. The exemplary different "Parts" that are included in this multi-part design may be an annular Lens edge 965C, a stabilization zone feature 970C, and an optic zone 975C are shown. A combination of discrete features producing a smooth and continuous convex cross-section 980C, and a plan view of a lens precursor design 900C are also shown.

Referring now to FIG. 9D, representations of a multi-part design concept of a non-smooth, non-continuous exemplary lens precursor 900D are depicted. Also included in FIG. 9D are cross-sectional representations of discrete features that may make up a lens precursor design. As may be observed the multi-part design may include a non-smooth, non-continuous convex cross-section 985D produced from a combination of discrete features. The plan view may also show a top down representation of this non-smooth, non-continuous round multi-part design Lens precursor 900D. Likewise, these representations may be made in 2-dimensional curved space illustrations. Further, an annular lens edge 965D feature, an optic zone 975D feature, and a combination of discrete features may be a non-continuous, non-smooth cross-section 985D as illustrated. Discontinuities can exist between the lens edge 965D and optic zone 975D.

The Digital Core-Break Concept

Referring again to FIGS. 1A, 1B, 1C, 1D, and 1E, numerous types of lens precursor features may have been combined to form the different designs. The associated target files may be constructed by combining a number of such different features together. Each of these combined features may be picked from one or both of catalog Items and non-catalog Items. A non-catalog Item in this case may indicate something that has been newly modeled or created for a specific lens design.

When a lens design may be formed by the combination of various lens precursor features a new lens precursor target design may be defined. However, it may be apparent that a great number of different lenses that are similar to the lens precursor target design may also be formed by assembling the same combination of precursor elements but whose parametric values may be different.

For example, the height of a particular stabilization design and/or lens design, the depth of a particular volumator feature may be varied creating similar but different designs. For some families of related designs, it may be desirable to keep select lens precursor features and/or select feature control parameters constant within a range of lens designs. When a subset of the feature control parameters for a collection of select lens precursor features are kept constant, while parameters on the other features may vary, the resulting family of designs may be referred to as a digital core break. Furthermore, one or more digital core break(s) may be present within a range of lens designs. It will be apparent from the teachings of the present disclosure to one skilled in the art that portions of the DMD files or DMD shows associated with different lens production in a digital core break, may be similar or identical to each other.

To further understand this concept of digital core break, consider a theoretical Acuvue Toric Precise Limited™, a system generated custom product. There are a large number of lenses in this product family with a variety of different values for their low order sphere power, cylinder power and cylinder axis correction that may be offered. The variation however may only cover a sphere power range of –3.00D to 0.00D and a cylinder power range of –2.00D to 0.00D. Continuing this example, these products within these various ranges may have identical lens edge, stabilization zone features and volumator features regardless of the sphere power, cylinder power and cylinder axis offered. Acuvue Toric Precise Limited™ therefore, may be characterized as only having one Digital Core Break.

A further example, may be that of Acuvue Toric Precise Plus™, a theoretical custom product whereby infinite parameters of only low order sphere power, cylinder power and cylinder axis correction may be offered in a large sphere power range of –20.00D to +20.00D and cylinder power range of –10.00D to 0.00D. Acuvue Toric Precise Plus™ may have three digital core breaks since within each sphere power range, for example, of –20.00D to –10.00D, –9.99D to +9.99D and +10.00D to +20.00D, lens edge, stabilization zone features and volumator features may be identical, but different in each of the three Digital Core Breaks.

An advanced target file may be created by starting with a base target file and modifying it to add characteristics. For example, a lens design to provide trefoil and coma correction together with corrections for a sphere power of –5.67D and a cylinder power of –4.56D at a cylinder axis of 78°, may be created by recalling catalog items for an Acuvue Toric Precise Plus™–5.67D/–4.56D×78° design, and incorporating desired high order correction components into these select recalled catalog items.

In general, there may be numerous manners and techniques within the scope of this inventive art to generate DMD files or DMD shows. The traditional methods, as depicted in FIG. 3, may be used.

Additionally, DMD files or DMD shows may also be generated by recalling catalog Items which then may be modified as needed. Previous DMD files or DMD shows may also be modified by numerous manners including adding in DMD files for new or modified features. Similar to target files, DMD files and/or DMD shows may be created from base, target files, DMD filed and/or DMD shows and incorporating instructions into them that may yield medium or high order correction into the fabricated lens. Examples of sample portions of DMD files are shown in both FIGS. 5 and 10.

Figure 11:
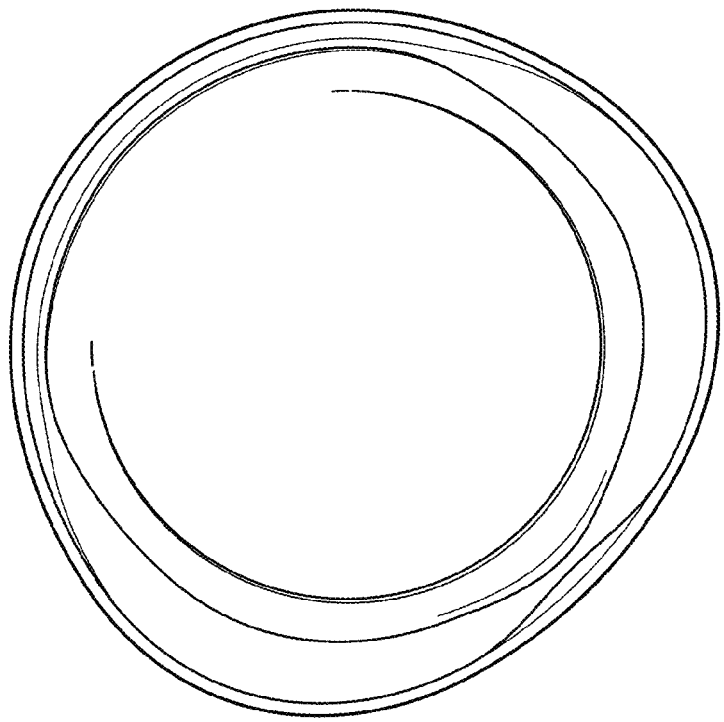
FIG. 11 illustrates an exemplary lens formed using a DMD file that may be implemented in some embodiments of the present invention, rotated by 180° around the y-axis and rotated counter-clockwise by 45° in an (x-y) plane.

In some further aspects, a lens precursor or lens precursor form may be fabricated via utilization of one or both of DMD files and DMD shows. For example, pertinent data to fabricate a desired lens precursor 105B or lens precursor form 100A may be contained in a single DMD file or DMD show, such as, instructions to generate lens edges, stabilization zone features, and optic zones. Additionally, for example, pertinent data to fabricate a desired lens precursor or lens precursor form may be contained in multiple DMD files or DMD shows such as, one DMD file or DMD shows may include instructions to generate lens edges and stabilization zone features, while a different DMD file or DMD show may contain instructions to generate optic zones and drain channel features. Further, pertinent data to fabricate desired lens precursors features within a desired lens precursor or lens precursor form can be distributed, for example, across one or both of DMD files and DMD shows. An example of a sample DMD show, rotated by 180° around the y-axis and rotated counter-clockwise by 45° in the x-y plane is illustrated in FIG. 11.

Figure 12:
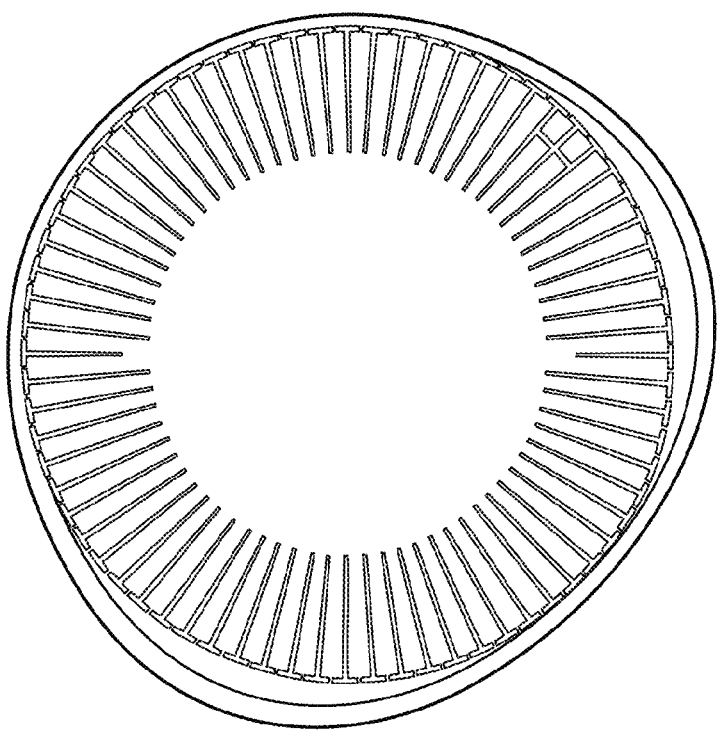
FIG. 12 illustrates an exemplary lens formed using a DMD file comprising circumferential drain channels.

An entire DMD file or DMD show, or portions thereof, may be utilized to overwrite a preceding DMD file or DMD show, or portions thereof. For example, a DMD file including of circumferential drain channel features may be superimposed on a preceding DMD file to allow drain channel features to be fabricated in a lens precursor without changing the preceding DMD file. An example of a sample DMD show plus a DMD file including circumferential drain channels is illustrated in FIG. 12. Another example may be to utilize a DMD file by superimposing it on a preceding DMD show to change one or both edge shape and profile of a lens precursor being fabricated, as illustrated in FIG. 13A and FIG. 13B.

Figure 13A:
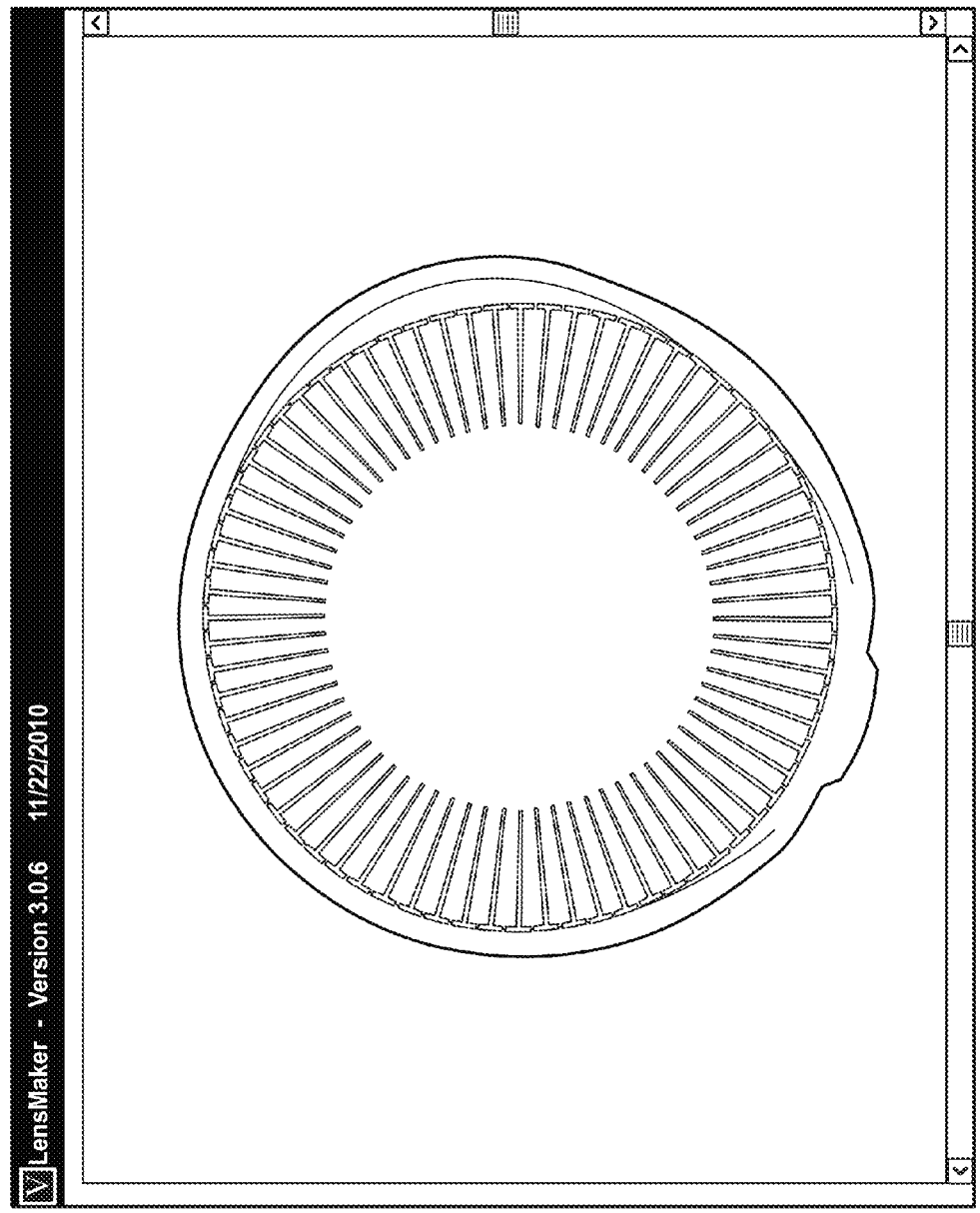
FIG. 13A illustrates an exemplary lens formed using a DMD file comprising circumferential drain channel instructions with a changed edge curvature instruction section.
Figure 13B:
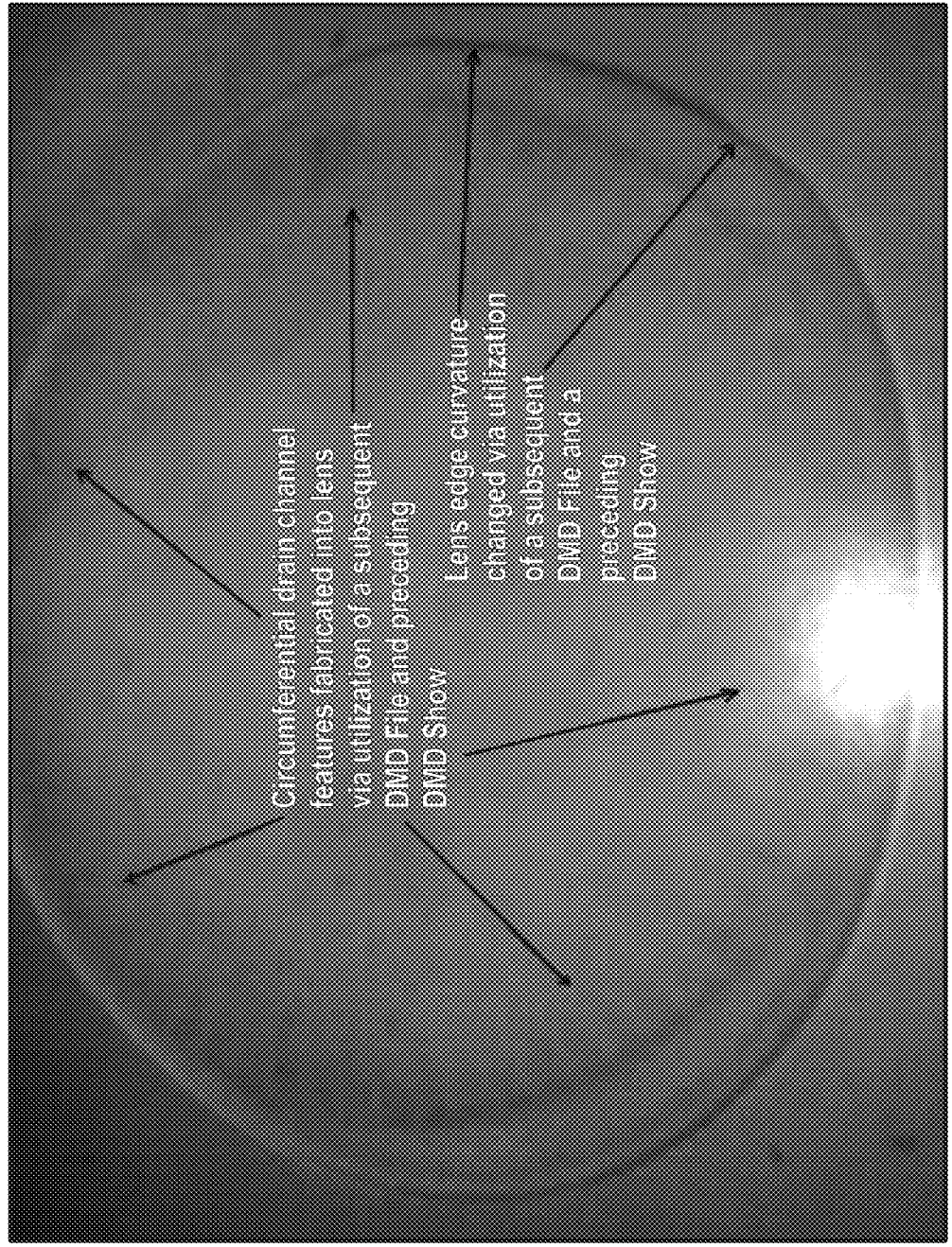
FIG. 13B illustrates a photograph of an exemplary non-rotationally symmetric lens including a flattened segment of a lens edge curvature and drain channels.

FIG. 13A illustrates an example of a sample DMD show with a DMD file containing circumferential drain channel instructions with a DMD file containing a changed edge curvature instruction section rotated by 180° around the y-axis and rotated counter-clockwise by 45° in an x-y plane as compared to the lens fabricated from the DMD show, a photograph of which is illustrated in FIG. 13B.

Complete or incomplete design target files, DMD files, DMD shows, DMD Iteration shows, catalog items, non-catalog items, etc., may be combined with other complete or incomplete design target files, DMD files, DMD shows, DMD Iteration shows, catalog Items, non-catalog Items, etc., and may be incorporated into DMD files and DMD shows from which a desired lens precursor may be fabricated. For example, if only a thickness description of an optic zone is passed to a fabrication facility, it may be converted into a DMD file and may be combined with another DMD file that may contain a lens edge and stabilization zone features. Therefore, a lens precursor may be fabricated without ever having specified a complete lens design or lens precursor design profile. For example, if neither individual, nor combined DMD files describe a complete surface profile, fluent lens reactive media may still connect an optic zone to stabilization zone features, thereby, completing a surface profile.

Figure 14:
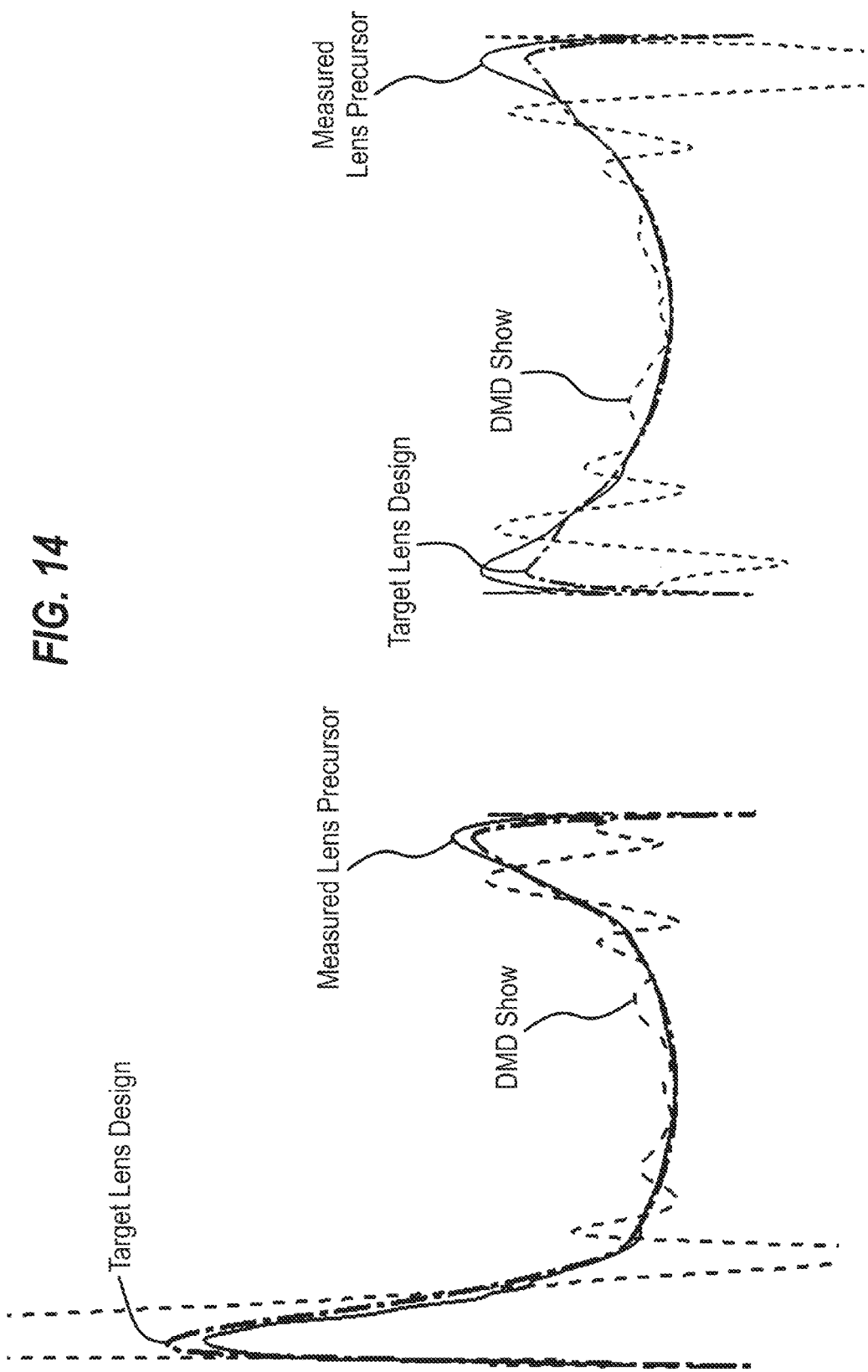
FIG. 14 illustrates an exemplary representation of two cross-sections (45° and) 135° of a target lens design, DMD show and measured lens precursor in flat space.

A lens precursor or lens precursor form may be measured for conformance to a design target file pre-, post-, or pre- and post-fixing processes. Resulting measurements may be utilized in an iterative loop and may enable a desired lens precursor 105 to be fabricated. An example of a representation of two cross-sections (at 45° and 135°) of a lens design, DMD shows, and measured lens precursor in flat space are illustrated in FIG. 14.

In some cases, a fabricated lens precursor may not precisely match a target file, or fall within specified acceptance criteria. For example, a fabricated lens precursor may include regions that may be one or more of the following: thicker than desired, thinner than desired, and at a desired target thickness. Several options may exist to fabricate a subsequent lens precursor that may be closer to a target file than its predecessor. For example, options may include utilizing one or more of a same DMD show with identical fabrication process conditions from a prior attempt, a modified DMD show with identical fabrication process conditions from a prior attempt, a same DMD show and modified fabrication process conditions, and a modified DMD show and modified fabrication process conditions.

One or both of a DMD file and a DMD show may be modified in many different ways, and may be based upon one or both of experience and differences between measured lens precursors and desired thickness maps. For example, a DMD file may be modified by one or more of changing select lens precursor feature design values and parameters within a file such as for optic zone, adding values and parameters for fabricating additional lens precursor features such as a moat feature, removing values and parameters of select fabricated lens precursor features such as drain channel features, and spatially redistributing values and parameters of select fabricated lens precursor features such as a volumator feature.

Specific examples have been described to illustrate the creation of lens precursor features, and the methods to create lenses and lens precursors with a variety of different features, and the nature and methods of forming DMD shows and DMD files to form lenses and lens precursors. These examples are for illustration and are not intended to limit the scope of the invention in any manner. Accordingly, the description and claims are intended to embrace all variations and alternatives that may be apparent to those skilled in the art.

What is claimed is:

1. A lens precursor form comprising:
a concave, optical quality first surface;
an opposing second surface having a substantially convex overall shape;
wherein the first and second surfaces are joined at a lens edge, wherein the lens edge defines the outer perimeter of the lens precursor form; and
a plurality of drain channel features, each comprising an elongate depression extending in a radial direction toward the lens edge, the drain channel features being placed side by side and configured to enable the flow of fluent lens reactive media across the lens precursor form.

2. The lens precursor form of claim 1 in which each drain channel feature is a continuous depression.

3. The lens precursor form of claim 1 in which each drain channel feature comprises discrete segmented depressions.

4. The lens precursor form of claim 1 in which the drain channel features radiate from a particular region of the lens precursor form so as to draw fluent lens reactive media away from that region.

5. The lens precursor form of claim 4 in which the drain channel features radiate in substantially all directions.

6. The lens precursor form of claim 4 in which the drain channel features radiate in a limited number of directions, thereby forming a fan-shaped drain sector.

7. The lens precursor form of claim 6 in which the fan-shaped drain sector has an included angle of between 2 and 360 degrees, for example between 30 and 120 degrees or between 60 and 90 degrees.

8. The lens precursor form of claim 7 in which the drain channel features further comprise circumferential drain channels at or towards their outer ends, at or towards their inner ends, or elsewhere, or in any combination of positions.

* * * * *